United States Patent
Ushiroda et al.

(10) Patent No.: US 11,653,826 B2
(45) Date of Patent: May 23, 2023

(54) MEDICAL OBSERVATION SYSTEM, CONTROL METHOD, AND PROGRAM IN WHICH ILLUMINATION LIGHT IS CONTROLLED IN ACCORDANCE WITH A USAGE STATE OF AN IMAGE SENSOR

(71) Applicant: Sony Olympus Medical Solutions Inc., Tokyo (JP)

(72) Inventors: Hiroshi Ushiroda, Tokyo (JP); Naobumi Okada, Tokyo (JP); Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 831 days.

(21) Appl. No.: 16/494,774

(22) PCT Filed: Feb. 16, 2018

(86) PCT No.: PCT/JP2018/005585
§ 371 (c)(1),
(2) Date: Sep. 17, 2019

(87) PCT Pub. No.: WO2018/179982
PCT Pub. Date: Oct. 4, 2018

(65) Prior Publication Data
US 2020/0037864 A1   Feb. 6, 2020

(30) Foreign Application Priority Data

Mar. 28, 2017 (JP) .............................. JP2017-063367
Jan. 25, 2018 (JP) .............................. JP2018-010962

(51) Int. Cl.
*A61B 1/06*   (2006.01)
*A61B 1/04*   (2006.01)
(Continued)

(52) U.S. Cl.
CPC ........ *A61B 1/0655* (2022.02); *A61B 1/00006* (2013.01); *A61B 1/000096* (2022.02);
(Continued)

(58) Field of Classification Search
CPC .................................................... G06T 7/0012
See application file for complete search history.

(56) References Cited

U.S. PATENT DOCUMENTS 4,356,534 A * 10/1982 Hattori ............... A61B 1/00006
362/276
6,511,422 B1 * 1/2003 Chatenever .......... A61B 1/0661
600/180
(Continued)

FOREIGN PATENT DOCUMENTS

DE     195 38 382 A1    4/1996
JP     2004-138818 A    5/2004
(Continued)

OTHER PUBLICATIONS

Extended European Search Report dated Mar. 12, 2020 in European Application No. 18777792.5.
(Continued)

*Primary Examiner* — John P Leubecker
(74) *Attorney, Agent, or Firm* — Xsensu LLP

(57) ABSTRACT

A medical observation system, a control method, and a program are provided, which are capable of easily reducing the possibility that illumination light directly enters an eye by accident. A medical observation system 1 includes: an imaging unit 21 that captures an object and generates an image signal; a light output unit 22 that outputs illumination light in a capturing direction of the imaging unit 21; a determining unit 942 that determines the usage state of the imaging unit 21; and an illumination controller 944 that
(Continued)

controls illumination light emitted by the light output unit 22 based on a determination result of the determining unit 942.

19 Claims, 13 Drawing Sheets

(51) Int. Cl.
    *A61B 1/00*         (2006.01)
    *G06T 7/00*         (2017.01)
    *G02B 21/12*       (2006.01)

(52) U.S. Cl.
    CPC ...... *A61B 1/00188* (2013.01); *A61B 1/00193* (2013.01); *A61B 1/042* (2013.01); *G06T 7/0012* (2013.01); *G02B 21/12* (2013.01)

(56) References Cited

U.S. PATENT DOCUMENTS

| | | | |
|---|---|---|---|
| 8,372,003 B2* | 2/2013 | St. George | A61B 1/05 600/118 |
| 2002/0013512 A1* | 1/2002 | Sendai | A61B 1/043 600/118 |
| 2010/0019170 A1* | 1/2010 | Hart | A61C 19/04 250/459.1 |
| 2011/0015528 A1* | 1/2011 | Kobayashi | A61B 1/00165 600/477 |
| 2011/0261184 A1* | 10/2011 | Mason | G02B 7/001 359/380 |
| 2012/0016230 A1* | 1/2012 | Kishima | A61B 1/045 600/425 |
| 2013/0016200 A1* | 1/2013 | Ovod | H04N 5/2352 348/E7.085 |
| 2014/0288365 A1* | 9/2014 | Henley | A61B 1/06 600/109 |
| 2017/0078583 A1* | 3/2017 | Haggerty | A61B 1/00071 |
| 2018/0140174 A1* | 5/2018 | Watanabe | A61B 1/044 |

FOREIGN PATENT DOCUMENTS

| | | |
|---|---|---|
| JP | 2004-337357 A | 12/2004 |
| JP | 2006-218204 A | 8/2006 |
| JP | 2009-118955 A | 6/2009 |
| JP | 2010207460 A | 9/2010 |
| TW | 201237541 A | 9/2012 |
| WO | 2016/152987 A1 | 9/2016 |

OTHER PUBLICATIONS

International Search Report and Written Opinion dated Apr. 17, 2018 for PCT/JP2018/005585 filed on Feb. 16, 2018, 6 pages including English Translation of the International Search Report.

\* cited by examiner

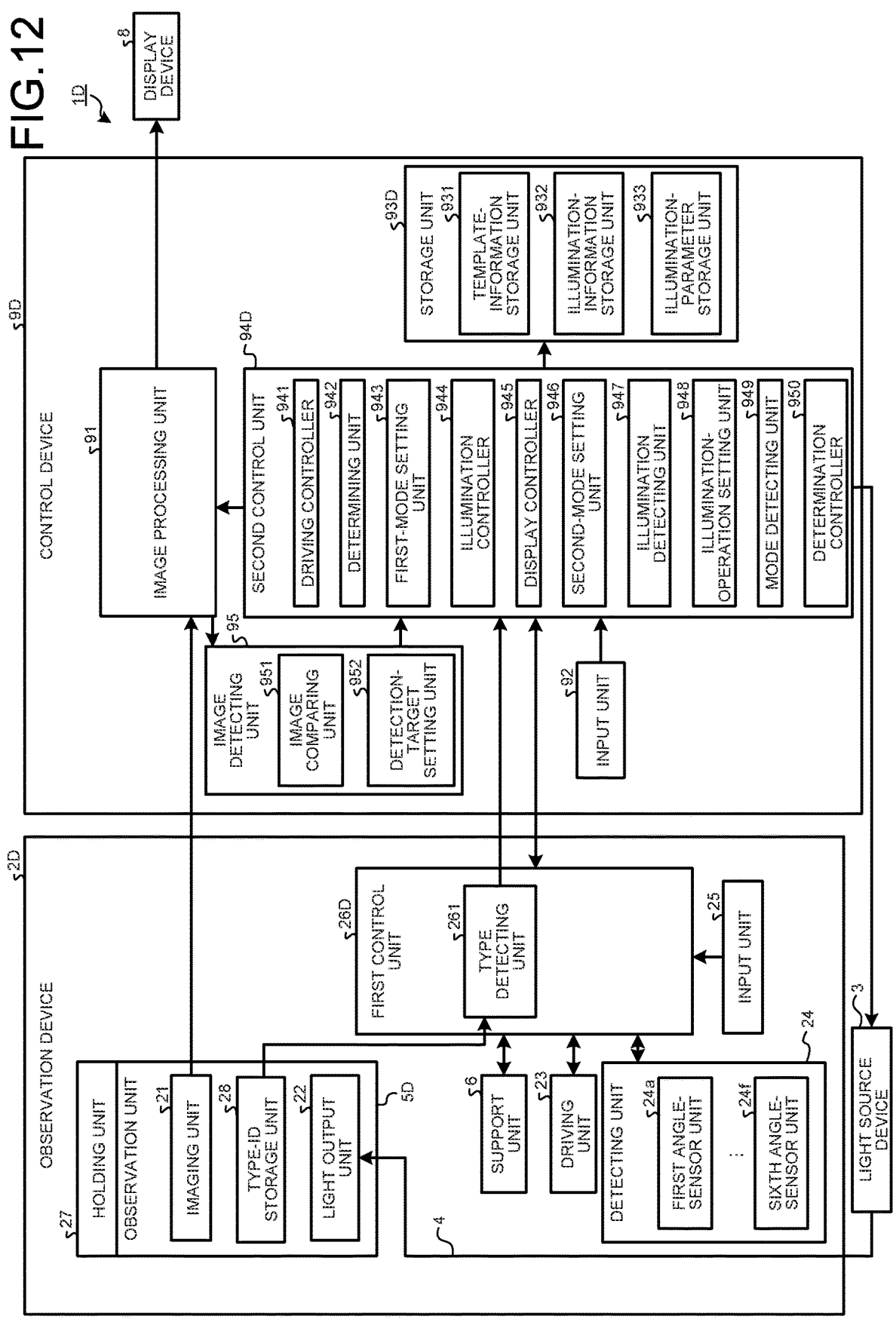

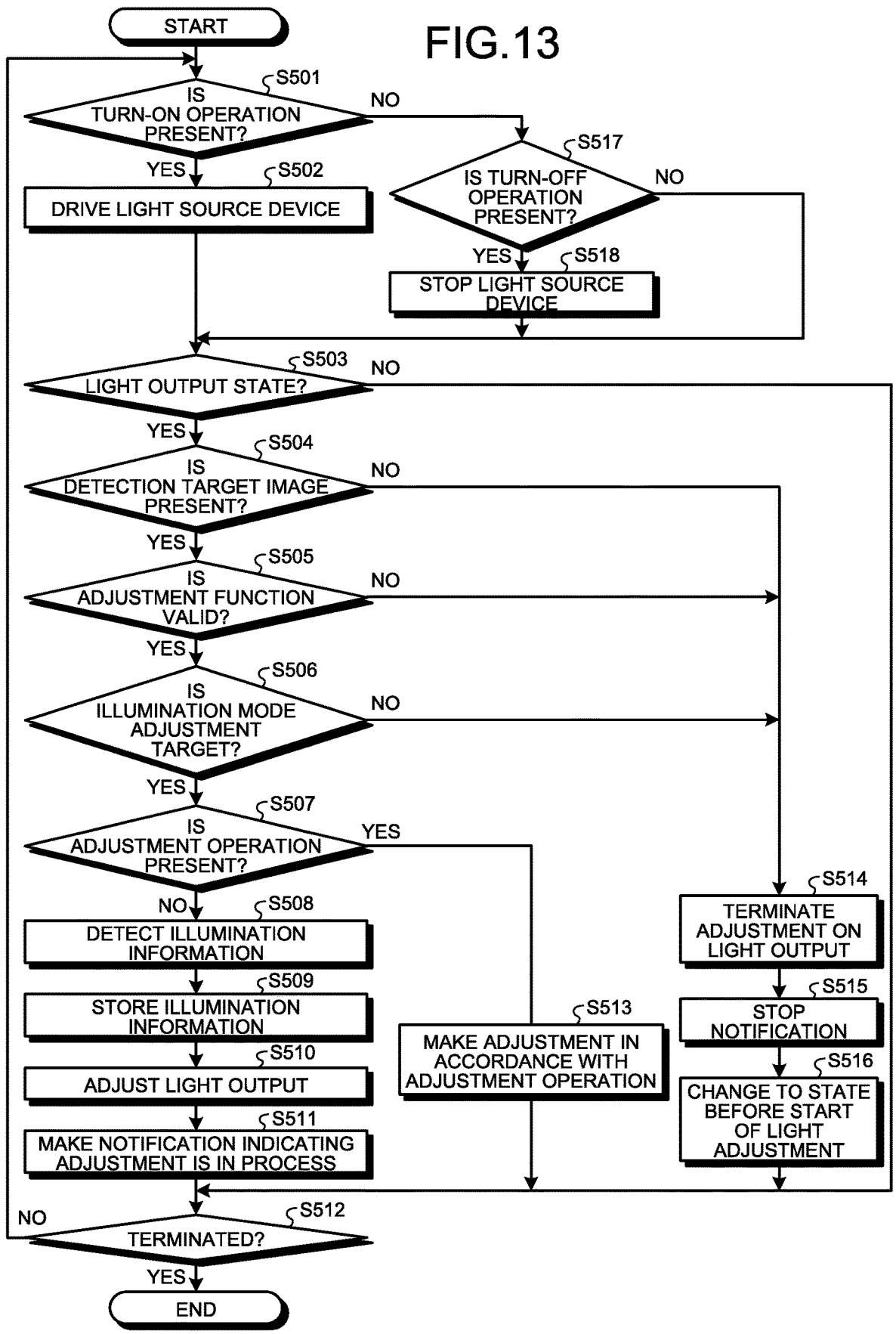

MEDICAL OBSERVATION SYSTEM, CONTROL METHOD, AND PROGRAM IN WHICH ILLUMINATION LIGHT IS CONTROLLED IN ACCORDANCE WITH A USAGE STATE OF AN IMAGE SENSOR

CROSS-REFERENCE TO RELATED APPLICATIONS

TECHNICAL FIELD

The present application is based on PCT filing PCT/JP2018/005585, filed Feb. 16, 2018, which claims priority to Japanese Patent Application Nos. JP 2017-063367, filed Mar. 28, 2017, and JP 2018-010962, filed Jan. 25, 2018, the entire contents of each are incorporated herein by reference.

The present invention relates to a medical observation system, a control method, and a program for capturing and observing an observed object.

BACKGROUND ART

Conventionally, surgical microscopes are used to observe a micro site, such as brain or heart, of a patient who is an observed object when a surgery is performed on the micro site. As an operator gives treatment to a micro site by using various types of medical devices or treatment tools, an improvement in the usability of the surgical microscope is required. For example, a movable housing containing an objective lens and an illumination optical system and arranged rotatably around the objective optical axis is disposed relative to a fixed housing having an observation optical system so that the observation direction is changed due to the rotation operation of the movable housing without changing the surgical field.

CITATION LIST

Patent Literature

Patent Literature 1: Japanese Laid-open Patent Publication No. 2004-337357

DISCLOSURE OF INVENTION

Technical Problem

Furthermore, a medical observation system such as surgical microscope or endoscope according to the above-described conventional technology 1 includes an illumination unit that emits illumination light to an object and has a function to optionally switch the illumination light of the illumination unit so as to be turned on and off. The illumination light used in the medical observation system has a higher intensity than the illumination light for typical indoor illumination, and therefore continuous direct viewing is not desirable.

Furthermore, with the medical observation system, in a situation where the observation position is changed, the illumination light is sometimes unnecessary; however, as the illumination light is constantly turned on, there is a possibility of the occurrence of a situation where the illumination light is accidentally emitted to the surrounding area and the illumination light enters an eye. In this case, it is considered that a user such as an operator turns off the illumination light when the observation position is changed; however, there is a problem in that the operation to turn off the illumination light each time causes inconvenience to the user.

The present disclosure has been made in consideration of the foregoing and has an object to provide a medical observation system, a control method, and a program that make it possible to easily reduce the possibility of the emission of illumination light to the surrounding area.

Solution to Problem

To solve the above-described problem and achieve the object, a medical observation system according to the present disclosure includes: an imaging unit configured to capture an object and generates an image signal; a light output unit configured to output illumination light in a capturing direction of the imaging unit; a determining unit configured to determine a usage state of the imaging unit; and an illumination controller configured to control illumination light emitted by the light output unit based on a determination result of the determining unit.

Moreover, the above-described medical observation system according to the present disclosure further includes: a support unit configured to hold the imaging unit and the light output unit and movably support the imaging unit and the light output unit; and a detecting unit configured to detect an angle formed between the capturing direction of the imaging unit and a previously set reference direction, wherein the determining unit is configured to determine whether the angle detected by the detecting unit falls outside a predetermined range, and the illumination controller is configured to control the illumination light emitted by the light output unit so as to be turned off or reduced when the determining unit determines falling outside the predetermined range.

Moreover, the above-described medical observation system according to the present disclosure further includes: a first-mode setting unit configured to set, in the medical observation system, any one of an electric visual-field move mode in which a capturing visual field of the imaging unit is changeable in upward, downward, leftward, and rightward directions by fixing a part of axes of joint units included in the support unit and moving a different axis in accordance with a command input from outside and an all-free mode in which the capturing direction of the imaging unit is changeable in a flexible manner; and a driving controller configured to control driving of the support unit in accordance with a setting of the first-mode setting unit, wherein when the first-mode setting unit has set the all-free mode in the medical observation system in a case where the determining unit determines falling outside the predetermined range, the illumination controller controls the illumination light emitted by the light output unit so as to be turned off or reduced.

Moreover, the above-described medical observation system according to the present disclosure further includes: a camera head including the imaging unit disposed at an inner side thereof; and a detecting unit configured to detect an angle formed between a capturing direction of the imaging unit and a previously set reference direction, wherein the determining unit is configured to determine whether the angle detected by the detecting unit falls outside a predetermined range, and when the determining unit determines falling outside the predetermined range, the illumination controller controls the illumination light emitted by the light output unit so as to be turned off or reduced.

Moreover, the above-described medical observation system according to the present disclosure further includes: a grasp detecting unit configured to detect whether the camera head is grasped by a user, wherein the determining unit is configured to determine whether the user is grasping the camera head in accordance with a detection result of the grasp detecting unit, and when the determining unit determines that the user is not grasping the camera head, the illumination controller controls the illumination light emitted by the light output unit so as to be turned off or reduced.

Moreover, the above-described medical observation system according to the present disclosure further includes: a detecting unit configured to detect a distance from an object captured by the imaging unit to a distal end part of the imaging unit, wherein the determining unit is configured to determine whether a distance detected by the detecting unit is more than a predetermined value, and when the determining unit determines being more than the predetermined value, the illumination controller controls the illumination light emitted by the light output unit so as to be turned off or reduced.

Moreover, the above-described medical observation system according to the present disclosure further includes: a first input unit configured to receive input of an operation to change an intensity of the illumination light emitted by the light output unit, wherein when the first input unit receives input of the operation in a case where the determining unit determines falling outside the predetermined range, the illumination controller performs control to change the intensity of the illumination light emitted by the light output unit.

Moreover, the above-described medical observation system according to the present disclosure further includes: a light source device configured to supply the illumination light to the light output unit; and a second input unit configured to receive input of a command to stop the light source device, wherein the illumination controller is configured to stop the illumination light supplied by the light source device when the second input unit receives input of a command to stop the light source device.

Moreover, in the above-described medical observation system according to the present disclosure, the light source device includes: a first light source unit configured to supply first illumination light having a first wavelength characteristic; and a second light source unit configured to supply second illumination light having a second wavelength characteristic different from the first wavelength characteristic, and the illumination controller is configured to control the second illumination light so as to be turned off or reduced when the light source device supplies at least any one of the first illumination light and the second illumination light to the light output unit in a case where the determining unit determines falling outside the predetermined range.

Moreover, in the above-described medical observation system according to the present disclosure, the light source device includes a blue light source configured to emit at least blue light having a blue wavelength band, and the illumination controller is configured to control the blue light so as to be turned off or reduced when the light source device supplies the blue light to the light output unit in a case where the determining unit determines falling outside the predetermined range.

Moreover, the above-described medical observation system according to the present disclosure further includes: a second-mode setting unit configured to set, in the medical observation system, any one of an automatic adjustment mode for performing control by the illumination controller and a manual adjustment mode that prohibits control by the illumination controller in accordance with a command input from outside, wherein the illumination controller is configured to control the illumination light emitted by the light output unit so as to be turned off or reduced when the second-mode setting unit has set the automatic adjustment mode in the medical observation system in a case where the determining unit determines falling outside the predetermined range.

Moreover, the above-described medical observation system according to the present disclosure further includes: a notifying unit configured to make a notification that the illumination controller controls the illumination light so as to be turned off or reduced.

Moreover, the above-described medical observation system according to the present disclosure further includes: a detecting unit configured to detect a distance from an object captured by the imaging unit to a distal end part of the imaging unit, wherein the determining unit is configured to determine whether a distance detected by the detecting unit is less than a predetermined value, and when the determining unit determines being less than the predetermined value, the illumination controller controls the illumination light emitted by the light output unit so as to be turned off or reduced.

Moreover, the above-described medical observation system according to the present disclosure further includes: an image detecting unit configured to detect a predetermined image pattern, which is previously set, from an image that corresponds to the image signal generated by the imaging unit, wherein the determining unit is configured to determine whether the image detecting unit has detected the image pattern, and when the determining unit determines that the image detecting unit has detected the image pattern, the illumination controller controls the illumination light emitted by the light output unit so as to be turned off or reduced.

Moreover, the above-described medical observation system according to the present disclosure further includes: a holding unit configured to removably hold any of observation units including at least any one of the imaging unit and the light output unit; a type detecting unit configured to detect a type of the observation unit attached to the holding unit; and a determination controller configured to switch a determination function of the determining unit to be enabled or disabled in accordance with a detection result of the type detecting unit.

Moreover, the above-described medical observation system according to the present disclosure further includes: an illumination-operation setting unit configured to set, in the light output unit, any of illumination modes in which illumination parameters including an intensity, an illumination range, and flashing/non-flashing of the illumination light output by the light output unit are different; a mode detecting unit configured to detect the illumination mode set by the illumination-operation setting unit; and a determination controller configured to switch a determination function of the determining unit to be enabled or disabled in accordance with a detection result of the mode detecting unit.

Moreover, the above-described medical observation system according to the present disclosure further includes: an illumination detecting unit configured to detect illumination information regarding an illumination state of the illumination light output by the light output unit; and an illumination-information storage unit configured to store the illumination information, wherein the illumination controller is configured to: store, in the illumination-information storage unit, the illumination information previously detected by the illumination detecting unit when the illumination light output by the light output unit is controlled to be reduced or turned off in accordance with a determination result of the determining unit; and perform control to reset the illumination state of the illumination light output by the light output unit based on the illumination information stored in the illumination-information storage unit when control for reducing or turning off the illumination light output by the light output unit is canceled.

Moreover, in the above-described medical observation system according to the present disclosure, the illumination controller is configured to perform control such that the illumination light is output with a lowest value of a light intensity when control for reducing or turning off the illumination light output by the light output unit is canceled in accordance with a determination result of the determining unit.

Moreover, a control method according to the present disclosure implemented by a medical observation system including an imaging unit that captures an object and generates an image signal; and a light output unit that outputs illumination light in a capturing direction of the imaging unit includes: a determining step of determining a usage state of the imaging unit, and an illumination control step of controlling illumination light emitted by the light output unit based on a determination result of the determining unit.

Moreover, a program according to the present disclosure causes a medical observation system including an imaging unit that captures an object and generates an image signal and a light output unit that outputs illumination light in a capturing direction of the imaging unit to execute: a determining step of determining a usage state of the imaging unit; and an illumination control step of controlling illumination light emitted by the light output unit based on a determination result of the determining unit.

Advantageous Effects of Invention

According to the present disclosure, there is an advantage such that it is possible to easily reduce the possibility of the emission of illumination light to the surrounding area.

BRIEF DESCRIPTION OF DRAWINGS

FIG. 12 is a block diagram that illustrates a functional configuration of the medical observation system according to a fifth embodiment.

FIG. 13 is a flowchart that illustrates the outline of a process performed by the medical observation system according to the fifth embodiment.

BEST MODE FOR CARRYING OUT THE INVENTION

An embodiment for carrying out the present invention (hereafter, referred to as "embodiment") is explained below in detail with reference to the drawings. Furthermore, the present invention is not limited to the following embodiment. Further, in each of the drawings referred to in the following explanation, the shape, the size, and the positional relationship are merely illustrated in a schematic manner so as to understand the details of the present invention. That is, the present invention is not limited to only the shape, the size, and the positional relationship illustrated in each of the drawings.

(First Embodiment)
[Schematic Configuration of the Medical Observation System]

Figure 1:
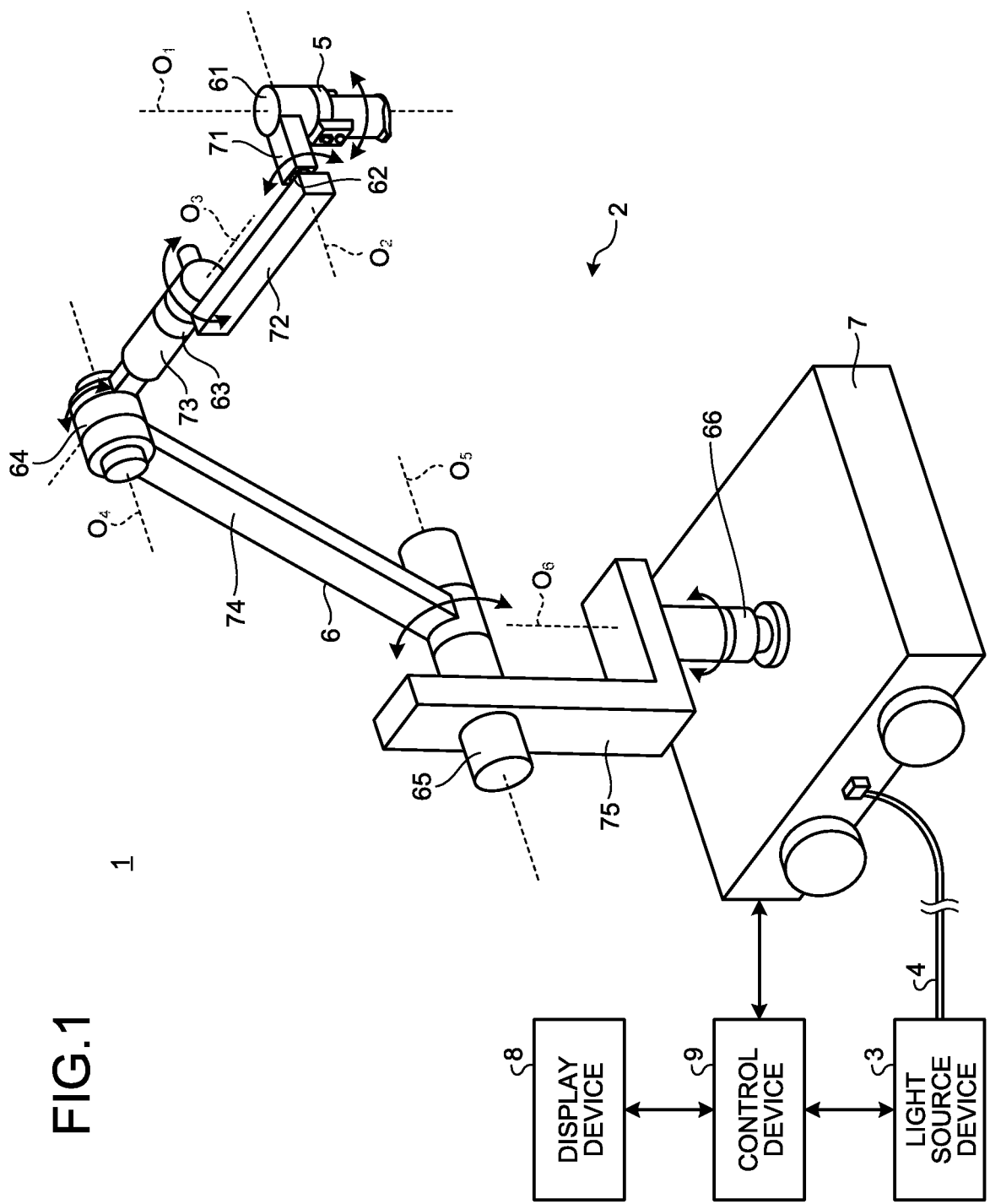
FIG. 1 is a diagram that illustrates the overall configuration of a medical observation system according to a first embodiment.

FIG. 1 is a diagram that illustrates the overall configuration of a medical observation system according to a first embodiment. A medical observation system 1 illustrated in FIG. 1 includes: a medical observation device 2 that has the function as a microscope for enlarging and observing a micro site of an observed object; a light source device 3 that supplies illumination light to the observation device 2 via a light guide 4 formed of an optical fiber, or the like; a display device 8 that displays an image captured by the observation device 2; and a control device 9 that controls operation of the medical observation system 1 in an integrated manner.

[Schematic Configuration of the Observation Device]

First, the schematic configuration of the observation device 2 is explained.

The observation device 2 includes: a microscope unit 5 that observes a micro site of the observed object, a support unit 6 that is connected to a proximal end part of the microscope unit 5 and rotatably supports the microscope unit 5; and a base unit 7 that rotatably holds the proximal end part of the support unit 6 and is capable of moving on the floor surface.

Figure 2:
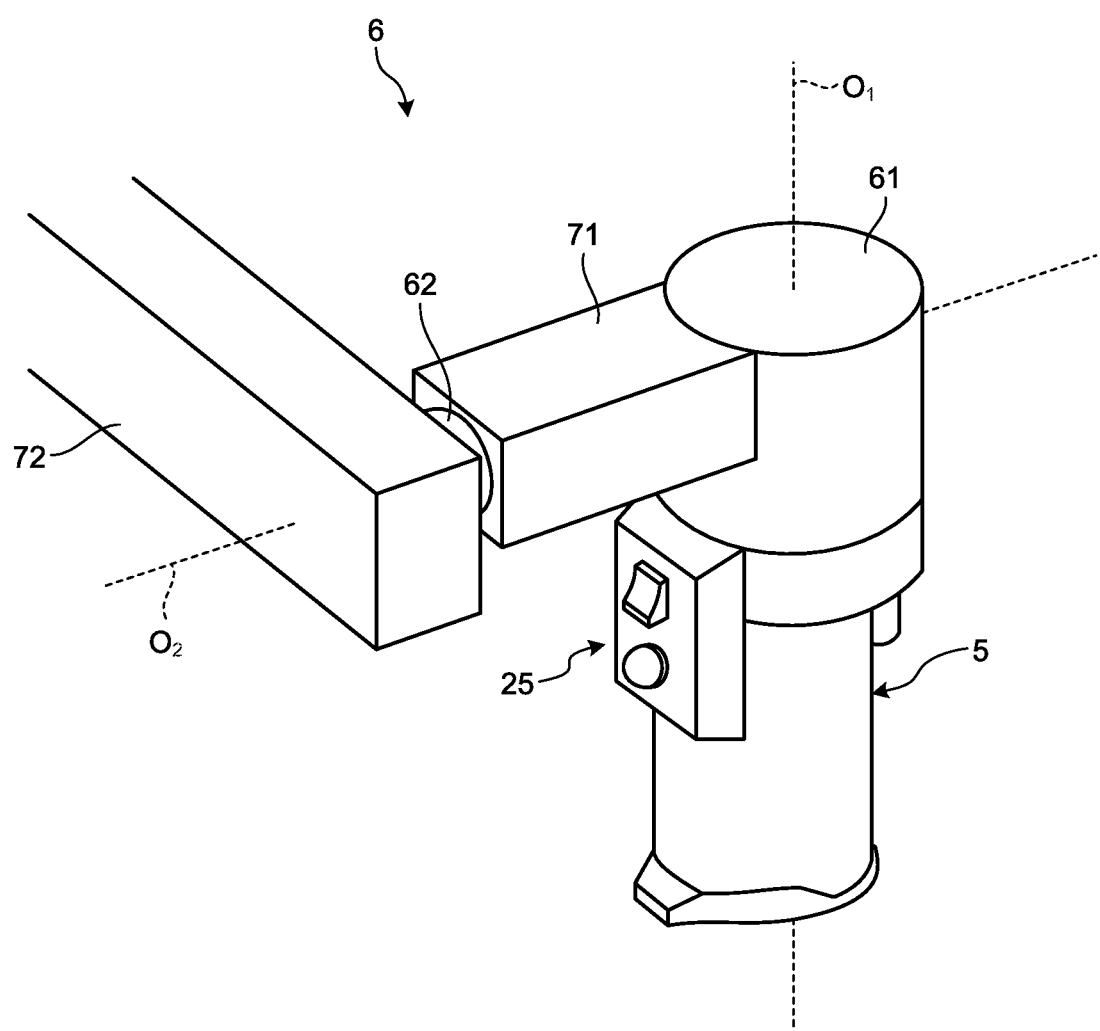
FIG. 2 is an enlarged perspective view that illustrates a configuration of a microscope unit and the periphery of the microscope unit according to the first embodiment.

FIG. 2 is an enlarged perspective view that illustrates a configuration of the microscope unit 5 and the periphery of the microscope unit 5. The microscope unit 5 has a cylindrical external appearance and, inside itself, includes an optical system having a zoom function and a focus function; an imaging element (not illustrated) that receives an object image formed by the optical system and conducts photoelectric conversion to generate an image signal; and a light output unit (not illustrated) that emits illumination light to the observed object. Furthermore, the side surface of the microscope unit 5 is provided with various switches forming an input unit 25 that receives input of an operation command of the observation device 2. An aperture surface of the microscope unit 5 at the lower end part is provided with a cover glass that protects an optical system, and the like, inside it (not illustrated). A user, such as an operator, moves the microscope unit 5, changes the angle of the microscope unit 5, changes the mode of the observation device 2, and performs zoom or focus operation by operating various switches while grasping the microscope unit 5. This allows a user to intuitively know the direction of the optical axis of the optical system or the central direction of the capturing visual field of the microscope unit 5 so that the microscope unit 5 may be easily moved to the desired position. Furthermore, the shape of the microscope unit 5 is not limited to a cylindrical shape but may be, for example, a polygonal and cylindrical shape.

With reference back to FIG. 1, the configuration of the observation device 2 is continuously explained.

In the support unit 6, sequentially from the distal end side (the side of the microscope unit 5), a first joint unit 61, a first arm unit 71, a second joint unit 62, a second arm unit 72, a third joint unit 63, a third arm unit 73, a fourth joint unit 64, a fourth arm unit 74, a fifth joint unit 65, a fifth arm unit 75, and a sixth joint unit 66 are connected.

The distal end side of the first joint unit 61 rotatably holds the microscope unit 5 around a first axis $O_1$ that coincides with the optical axis of the microscope unit 5, and the proximal end side is held by the first arm unit 71 in a state where it is secured to the distal end part of the first arm unit 71.

The distal end side of the second joint unit 62 rotatably holds the first arm unit 71 around a second axis $O_2$ perpendicular to the first axis $O_1$, and the proximal end side is held by the second arm unit 72. In the same manner, the distal end sides of the third joint unit 63 to the sixth joint unit 66 rotatably hold the second arm unit 72 to the fourth arm unit 74, respectively, and the proximal end sides are held in a state where they are secured to the distal end parts of the third arm unit 73 to the fifth arm unit 75, respectively.

The distal end side of the sixth joint unit 66 rotatably holds the fifth arm unit 75, and the proximal end side is held in a state where it is secured to the base unit 7.

The second arm unit 72 to the fifth arm unit 75 are rotatable around a third axis $O_3$ to a sixth axis $O_6$, respectively, as rotation axes. A fourth axis $O_4$ and a fifth axis $O_5$ are parallel to the second axis $O_2$. The third axis $O_3$ and the fourth axis $O_4$ are perpendicular to each other, and the fifth axis $O_5$ and the sixth axis $O_6$ are perpendicular to each other.

Each of the first joint unit 61 to the sixth joint unit 66 includes an angle sensor (not illustrated) that functions as an electromagnetic brake (not illustrated) and a detecting unit that prohibits the rotation of the microscope unit 5 and the first arm unit 71 to the fifth arm unit 75 at the respective distal end sides. The electromagnetic brake is released in accordance with the input of a release command received by the input unit 25 of the microscope unit 5. When the electromagnetic brake is released, the microscope unit 5 and the first arm unit 71 to the fifth arm unit 75 enter a rotatable state with respect to the first joint unit 61 to the sixth joint unit 66, respectively. Hereafter, the state where the microscope unit 5 and the first arm unit 71 to the fifth arm unit 75 are rotatable with respect to the first joint unit 61 to the sixth joint unit 66 is referred to as the all-free mode. Furthermore, instead of the electromagnetic brake, an air brake is also applicable.

The first joint unit 61 to the sixth joint unit 66 are provided with an actuator (not illustrated) that assists the rotation of the microscope unit 5 and the first arm unit 71 to the fifth arm unit 75, respectively. Furthermore, the first joint unit 61 to the sixth joint unit 66 are provided with various sensors (not illustrated) that function as a detecting unit that detects at least part of the position, the speed, the acceleration, the rotation angle, the rotating velocity, the rotation acceleration, the generated torque, and the like, of each joint unit.

The support unit 6 having the above configuration enables three degrees of freedom in translation and three degrees of freedom in rotation, six degrees of freedom in movement in total, in the microscope unit 5. Further, in the support unit 6 according to the first embodiment, all the actuators do not need to be provided, and changes may be made as needed. For example, a part of the first arm unit 71 to the fifth arm unit 75 of the support unit 6 may be provided with an actuator.

The light source device 3 supplies illumination light to the observation device 2 via the light guide 4 under the control of the control device 9. The light source device 3 is configured by using a discharge lamp such as xenon lamp or metal halide lamp, a solid light emitting element such as LED (Light Emitting Diode) or LD (Laser Diode), a light emitting member such as a laser light source or a halogen lamp, and the like.

The display device 8 displays display images (video signal) generated by the control device 9 and various types of information regarding the medical observation system. The display device 8 is configured by using a liquid crystal, an organic EL (Electro Luminescence), or the like. Furthermore, the monitor size of the display device 8 is equal to or more than 31 inches, preferably equal to or more than 55 inches. Moreover, according to the first embodiment, although the display device 8 is configured with the monitor size of equal to or more than 31 inches, this is not a limitation, and the monitor size may be different as long as the monitor size enables the display of images having a resolution of, for example, equal to or more than 2 megapixels (e.g., a resolution of what is called 2K with 1920×1080 pixels), preferably a resolution of equal to or more than 8 megapixels (e.g., a resolution of what is called 4K with 3840×2160 pixels), more preferably a resolution of equal to or more than 32 megapixels (e.g., a resolution of what is called 8K with 7680×4320 pixels). It is obvious that the display device 8 may be a monitor capable of displaying 3D images.

The control device 9 controls each unit of the medical observation system 1 in an integrated manner. The control device 9 is implemented by using a general-purpose processor, such as a CPU (Central Processing Unit), or a dedicated processor such as various arithmetic circuits performing a specific function, e.g., ASIC (Application Specific Integrated Circuit). Furthermore, it may be configured by using an FPGA (Field Programmable Gate Array: not illustrated) that is one type of programmable integrated circuit. Moreover, when it is configured by using an FPGA, a memory that stores configuration data may be provided, and an FPGA, which is a programmable integrated circuit, may be configured with configuration data that is read from the memory. Further, the detailed configuration of the control device 9 is described later.

[Functional Configuration of the Medical Observation System]

Figure 3:
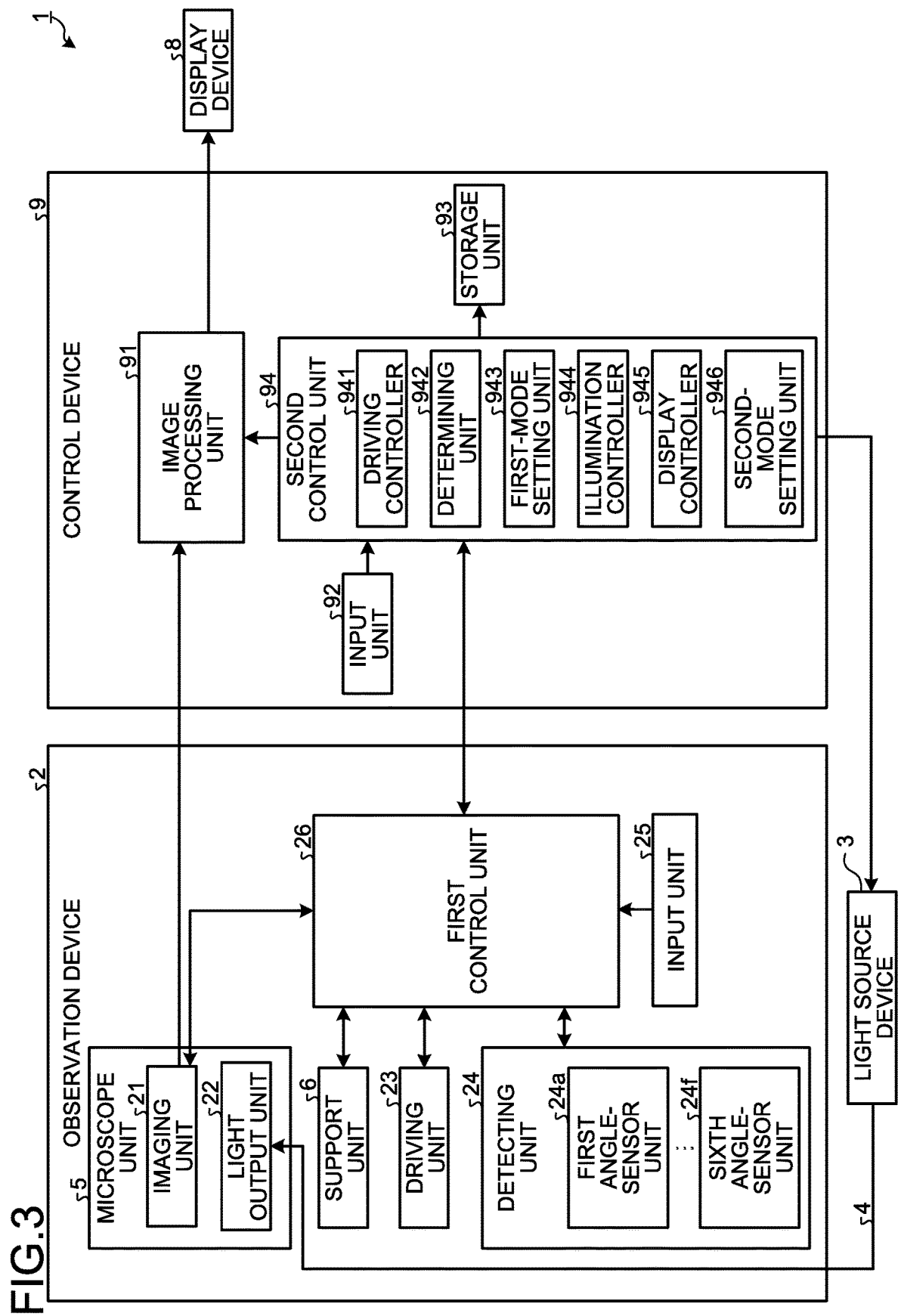
FIG. 3 is a block diagram that illustrates a functional configuration of the medical observation system according to the first embodiment.

Next, a functional configuration of the above-described medical observation system 1 is explained. FIG. 3 is a block diagram that illustrates a functional configuration of the medical observation system 1.

[Configuration of the Observation Device]

First, the functional configuration of the observation device 2 is explained.

The observation device 2 includes the microscope unit 5, the support unit 6, a driving unit 23, a detecting unit 24, the input unit 25, and a first control unit 26.

The microscope unit 5 includes: an imaging unit 21 that generates an image signal by enlarging and capturing an image of the observed object, which is the photographic subject; and a light output unit 22 that emits the illumination light supplied from the light source device 3 to the observed object.

The imaging unit 21 includes: an optical system that has the zoom and the focus functions; and an imaging element that receives an image of the observed object formed by the optical system and conducts photoelectric conversion to generate an image signal. The imaging element is configured by using a CCD (Charge Coupled Device) or a CMOS (Complementary Metal Oxide Semiconductor). Imaging signals generated by the imaging unit 21 are transmitted to the control device 9 via a transmission cable. Furthermore, E/O conversion may be conducted on imaging signals generated by the imaging unit 21 so that optical signals are transmitted to the control device 9. Furthermore, it is appropriate that the imaging unit 21 has a resolution of, for example, equal to or more than 2 megapixels (e.g., a resolution of what is called 2K with 1920×1080 pixels), preferably a resolution of equal to or more than 8 megapixels (e.g., a resolution of what is called 4K with 3840×2160 pixels), more preferably a resolution of equal to or more than 32 megapixels (e.g., a resolution of what is called 8K with 7680×4320 pixels). Furthermore, the imaging unit 21 may generate 3D image signals by generating two image signals with two imaging elements for which a predetermined disparity is set.

The light output unit 22 includes an illumination optical system configured by using one or more lenses. The light output unit 22 emits the illumination light supplied from the light source device 3 via the light guide 4 in the same direction as the capturing direction of the imaging unit 21. Furthermore, for the light output unit 22, optical transmission of the light guide, or the like, may be omitted by providing an LED (Light Emitting Diode), a laser light source, or the like, in the microscope unit 5.

The support unit 6 rotatably supports the microscope unit 5 as in the above-described FIG. 1 and FIG. 2. The support unit 6 enables three degrees of freedom in translation and three degrees of freedom in rotation, six degrees of freedom in movement in total, in the microscope unit 5.

The driving unit 23 includes an electromagnetic brake and an actuator provided in each of the first joint unit 61 to the sixth joint unit 66 described above. The electromagnetic brake is released responsive to the input of a release command received by the input unit 25 during an operation in the all-free mode. The actuator operates responsive to a control signal transmitted from the control device 9, described later, in accordance with a state detection result by the detecting unit 24.

The detecting unit 24 sequentially detects the state information on the observation device 2. The state information on the observation device 2 includes information about the position, the focus, and the zoom of the imaging unit 21, information about at least a part of the position, the speed, the acceleration, the rotation angle, the rotating velocity, the rotation acceleration, and the generated torque of the first joint unit 61 to the sixth joint unit 66, information about at least a part of the position, the speed, and the acceleration of the first arm unit 71 to the fifth arm unit 75, and information about operation in an electric visual-field move mode (a pivot operation mode or an XY operation mode), the all-free mode, or the like. The detecting unit 24 includes various sensors for detecting the above information. Specifically, the detecting unit 24 includes a first angle-sensor unit 24a to a sixth angle-sensor unit 24f that detect the angles of the first arm unit 71 to the fifth arm unit 75 (the first axis $O_1$ to the sixth axis $O_6$), respectively, with respect to the reference direction. Here, the reference direction is the direction of gravitational force (vertical direction) when, as a reference, the observation device 2 (the first arm unit 71 to the fifth arm unit 75) is located on the floor. That is, according to the first embodiment, an explanation is given by using the reference direction as 0 degrees. It is obvious that the reference direction is changed depending on the area where the observation device 2 (the first arm unit 71 to the fifth arm unit 75) is installed. For example, when the observation device 2 (the first arm unit 71 to the fifth arm unit 75) is suspended from the ceiling that is an installation area, the reference direction is changed by 180 degrees as compared to the case where it is installed on the floor. Furthermore, when the observation device 2 (the first arm unit 71 to the fifth arm unit 75) is fixed at a wall (fixed at a vertical wall) that is an installation area, the reference direction is changed by 90 degrees as compared to the case where it is installed on the floor. Moreover, when the direction of the first axis $O_1$ detected by the first angle-sensor unit 24a is the same as the capturing direction of the imaging unit 21, the first angle-sensor unit 24a may be omitted.

Here, the electric visual-field move mode (XY operation mode) is an operation mode in which the capturing visual field of the imaging unit 21 is changeable in upward, downward, leftward, and rightward directions by fixing a part of the axes of the joint units included in the support unit 6 and moving a different axis. Specifically, the electric visual-field move mode (XY operation mode) is an operation mode in which the capturing visual field of the imaging unit 21 is changeable in upward, downward, leftward, and rightward directions by fixing the fourth axis $O_4$ to the sixth axis $O_6$ and electrically operating only the second axis $O_2$ and the third axis $O_3$.

Furthermore, the pivot operation mode is a pivot operation in which the microscope unit 5 is moved due to the movement of the support unit 6 on the conical surface having its vertex at a single point in the central direction of the capturing visual field of the imaging unit 21 when it is fixed at the single point, and it is also called a point lock operation. The pivot for the pivot operation mode is the central axis in the height direction of the cone. During the pivot operation mode, the distance between the fixed point and the imaging unit 21 is kept constant. For a surgery, for example, a surgical site is selected as the above-described fixed point. This pivot operation mode allows a surgical site to be observed in the same distance at a different angle; therefore, a user may determine a surgical site with more accuracy.

The input unit 25 receives input of operation commands for the imaging unit 21 and the driving unit 23. The input unit 25 includes an arm operation switch for receiving input to designate the all-free mode by releasing the electromagnetic brake included in the driving unit 23, a focus switch and a zoom switch for receiving input to designate focus and zoom operations of the imaging unit 21, an electric visual-field move mode switch for receiving input to designate the electric visual-field move mode, and a power assist switch for receiving input to designate a power assist mode. As illustrated in FIG. 2, various switches, buttons, and the like, included in the input unit 25 are disposed on the side surface of the microscope unit 5. Here, FIG. 2 illustrates a part of various switches, buttons, and the like, included in the input unit 25. Moreover, according to the first embodiment, the input unit 25 functions as a first input unit.

The first control unit 26 controls operations of the imaging unit 21 and the driving unit 23 responsive to input of an operation command received by the input unit 25 or an operation command input from the control device 9 described later. Furthermore, the first control unit 26 controls the observation device 2 in an integrated manner in cooperation with a second control unit 94, described later, of the control device 9. The first control unit 26 is configured by using a CPU (Central Processing Unit), an ASIC (Application Specific Integrated Circuit), or the like.

[Configuration of the Control Device]

Next, a functional configuration of the control device 9 is explained.

The control device 9 includes an image processing unit 91, an input unit 92, a storage unit 93, and the second control unit 94.

The image processing unit 91 conducts E/O conversion on imaging signals that are optical signals transmitted from the observation device 2 and then performs predetermined image processing, thereby generating a display image (video signal) for display, which are to be displayed on the display device 8. Here, image processing includes various types of image processing, such as color correction, color enhancement, outline enhancement, or mask processing. The image processing unit 91 is configured by using a CPU, an ASIC, or an FPGA.

The input unit 92 is implemented by using a user interface such as a keyboard, mouse, or touch panel, and it receives input of various types of information. Furthermore, according to the first embodiment, the input unit 92 functions as a second input unit.

The storage unit 93 is configured by using a semiconductor memory such as a flash memory or a DRAM (Dynamic Random Access Memory), and it temporarily stores various programs and data in processing executed by the medical observation system 1.

The second control unit 94 controls each unit of the medical observation system 1 in an integrated manner. The second control unit 94 is implemented by using a general-purpose processor, such as a CPU, including an internal memory (not illustrated) that stores a program, or a dedicated processor, such as various arithmetic circuits, executing a specific function, e.g., ASIC. Furthermore, it may be configured by using an FPGA that is one type of programmable integrated circuit. Moreover, when it is configured by using an FPGA, a memory that stores configuration data may be provided, and an FPGA, which is a programmable integrated circuit, may be configured with configuration data that is read from the memory. The second control unit 94 includes a driving controller 941, a determining unit 942, a first-mode setting unit 943, an illumination controller 944, a display controller 945, and a second-mode setting unit 946.

The driving controller 941 controls driving of the support unit 6. Specifically, the driving controller 941 controls driving of each actuator or magnetic brake of the support unit 6 in accordance with the type of operation received by the input unit 25 or the input unit 92.

The determining unit 942 determines the usage state of the imaging unit 21. Specifically, the determining unit 942 determines whether the angle detected by the detecting unit 24 falls outside a predetermined range. For example, the determining unit 942 determines whether the angle formed between the reference direction and the capturing direction of the imaging unit 21, detected by the first angle-sensor unit 24a, falls outside the predetermined range. Here, falling outside the predetermined range refers to being an angle with which the capturing direction of the imaging unit 21 is more than horizontal. Obviously, there is a patient for surgery. In many cases, a patient lies on a surgical bed. Conversely, a user such as an operator performs surgery and gives treatment to the patient at a standing position or a seated position. Furthermore, the user's hand extends downward obliquely from above with respect to the patient, extends horizontally in rare cases, and extends upward obliquely from underneath in extremely rare cases. As the site captured by the observation device 2 is basically a treated site of the patient, the capturing direction of the imaging unit 21 is the same as the direction of the operator's hand. Moreover, in a surgery room, there is also an assistant, a nurse, an anesthetist, a visitor, and the like, as well as a patient and a user. They are present at a standing position or a seated position around the surgical bed, and their faces are often located at a position higher than the patient. In such a situation, when the capturing direction of the imaging unit 21 (the irradiation direction of the light output unit 22) is more than horizontal, there is a high possibility that the illumination light is emitted to the faces of the surrounding people. Therefore, according to the first embodiment, the determining unit 942 determines whether the capturing direction of the imaging unit 21 falls outside the predetermined range, i.e., the capturing direction of the imaging unit 21 is more than horizontal, based on a detection result of the detecting unit 24. Moreover, although the determining unit 942 determines whether the capturing direction of the imaging unit 21 is more than horizontal (equal to or more than 90 degrees) according to the first embodiment, this is not a limitation, and the user may optionally change it with an operation on the input unit 92.

In accordance with a command input from the input unit 25 or the input unit 92, the first-mode setting unit 943 sets, in the medical observation system 1, any one of the electric visual-field move mode (the pivot operation mode) in which the capturing visual field of the imaging unit 21 is changeable due to a movement of the support unit 6 while the single point in the central direction of the capturing visual field of the imaging unit 21 is fixed, the electric visual-field move mode (the XY operation mode) in which the capturing visual field of the microscope unit 5 is changeable by operating only the second axis $O_2$ and the third axis $O_3$ of the support unit 6, and the all-free mode in which the capturing direction of the imaging unit 21 is flexibly changeable.

The illumination controller 944 controls the illumination light output by the light output unit 22 based on a determination result of the determining unit 942. Specifically, the illumination controller 944 controls the light source device 3 based on a determination result of the determining unit 942, thereby controlling the illumination light output by the light output unit 22. For example, the illumination controller 944 controls the light source device 3 so as to turn off or reduce the illumination light output by the light output unit 22 when the determining unit 942 determines that the angle formed between the reference direction and the capturing direction of the imaging unit 21, detected by the detecting unit 24, falls outside the predetermined range.

The display controller 945 controls the image processing unit 91, thereby controlling the display mode of the display device 8. Specifically, the display controller 945 superimposes the information indicating that the observation device 2 is adjusting the light output on the display image on the display device 8, thereby making a notification.

The second-mode setting unit 946 sets, in the medical observation system 1, any one of the automatic adjustment mode for performing the control by the illumination controller 944 and the manual adjustment mode for prohibiting the control by the illumination controller 944 in accordance with a command input from the input unit 25 or the input unit 92.

[Process of the Medical Observation System]

Next, a process of the medical observation system 1 is explained.

Figure 4:
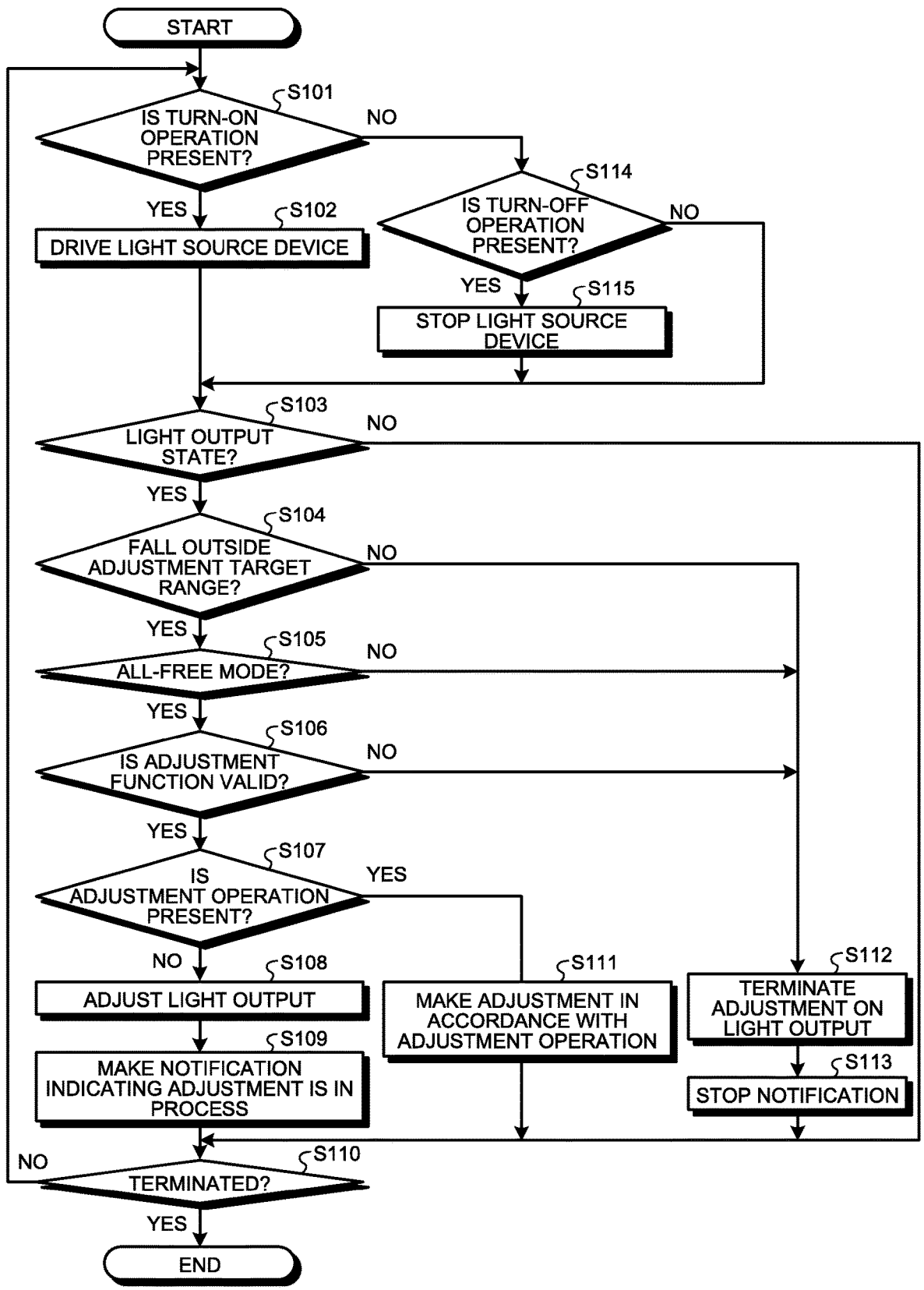
FIG. 4 is a flowchart that illustrates the outline of a process performed by the medical observation system according to the first embodiment.

FIG. 4 is a flowchart that illustrates the outline of a process performed by the medical observation system 1.

As illustrated in FIG. 4, when the input unit 92 first has received input of a turn-on operation for giving a command to the light source device 3 so as to be turned on (Step S101: Yes), the illumination controller 944 drives the light source device 3 (Step S102). Thus, the light source device 3 supplies illumination light to the observation device 2.

Then, the determining unit 942 determines whether the light output unit 22 is in a light output state (Step S103). Specifically, the determining unit 942 determines whether the light source device 3 is in an activated state, thereby determining whether the light output unit 22 is in a light output state. When the determining unit 942 determines that the light output unit 22 is in a light output state (Step S103: Yes), the medical observation system 1 proceeds to Step S104 described later. Conversely, the determining unit 942 determines that the light output unit 22 is not in a light output state (Step S103: No), the medical observation system 1 proceeds to Step S110 described later.

At Step S104, the determining unit 942 determines whether the imaging unit 21 falls outside the adjustment target range. Specifically, the determining unit 942 determines whether the angle formed between the reference direction and the capturing direction of the imaging unit 21 is more than horizontal (e.g., equal to or more than 90 degrees such that the capturing direction and the emitting direction of the microscope unit 5 is a direction right above) based on the detection angle detected by each of the first angle-sensor unit 24*a* to the sixth angle-sensor unit 24*f*. When the determining unit 942 determines that the imaging unit 21 falls outside the adjustment target range (Step S104: Yes), the medical observation system 1 proceeds to Step S105 described later. Conversely, when the determining unit 942 determines that the imaging unit 21 does not fall outside the adjustment target range (Step S104: No), the medical observation system 1 proceeds to Step S112 described later.

At Step S105, the determining unit 942 determines whether the all-free mode has been set to the observation device 2. Specifically, the determining unit 942 determines whether the first-mode setting unit 943 has set the mode of the observation device 2 to the all-free mode in accordance with an operation on the input unit 25. The user sets the all-free mode to largely move the capturing direction and, on the other hand, sets the electric visual-field move mode to slightly move the capturing direction. Therefore, in the all-free mode, the user hardly provides treatment in the course of moving the microscope unit 5, and the illumination light may be unnecessary or minimum; however, as the capturing direction of the imaging unit 21 is largely changeable, there is a possibility that the illumination light is accidentally emitted to the surrounding people. On the other hand, in the electric visual-field move mode, as micro adjustment is often conducted while treatment is provided, the illumination light is necessary, and micro direction adjustment is conducted while the treated site is captured; therefore, there is no possibility that the illumination light is emitted to the surrounding people. For this reason, the determining unit 942 determines whether the all-free mode has been set to the observation device 2, and when the all-free mode has been set to the observation device 2, the illumination controller 944 performs the control as described later. Specifically, when the determining unit 942 determines that the all-free mode has been set to the observation device 2 (Step S105: Yes), the medical observation system 1 proceeds to Step S106 described later. Conversely, when the determining unit 942 determines that the all-free mode has not been set to the observation device 2 (Step S105: No), the medical observation system 1 proceeds to Step S112 described later.

At Step S106, the determining unit 942 determines whether the automatic adjustment mode for automatically adjusting the illumination light output by the light output unit 22 is valid in the observation device 2. Specifically, the determining unit 942 determines whether any one of the automatic adjustment mode for automatically adjusting the illumination light output by the light output unit 22 and the manual adjustment mode for prohibiting the control by the illumination controller 944 is set in the second-mode setting unit 946 in accordance with an operation of the input unit 92. When the determining unit 942 determines that the adjustment function mode is valid (Step S106: Yes), the medical observation system 1 proceeds to Step S107 described later. Conversely, when the determining unit 942 determines that the adjustment function mode is not valid (Step S106: No), the medical observation system 1 proceeds to Step S112 described later.

At Step S107, the determining unit 942 determines whether the user has performed an operation to adjust the light output, output by the light output unit 22, via the input unit 25. When the determining unit 942 determines that the operation to adjust the light output, output by the light output unit 22, has been performed (Step S107: Yes), the medical observation system 1 proceeds to Step S111 described later. Conversely, when the determining unit 942 determines that the operation to adjust the light output, output by the light output unit 22, has not been performed (Step S107: No), the medical observation system 1 proceeds to Step S108 described later.

At Step S108, the illumination controller 944 controls the illumination light supplied from the light source device 3, thereby adjusting the light output that is output by the light output unit 22. For example, the illumination controller 944 controls the light source device 3 to decrease the intensity of the illumination light supplied from the light source device 3, thereby making an adjustment to reduce the light output by the light output unit 22. In this case, the illumination controller 944 may gradually decrease the intensity of the illumination light supplied from the light source device 3 based on the detection angle detected by each of the first angle-sensor unit 24*a* to the sixth angle-sensor unit 24*f* so as to adjust the intensity of the light output by the light output unit 22. For example, the illumination controller 944 gradually decreases the intensity of the illumination light supplied from the light source device 3 during a time period in which, when the reference direction (0 degrees) of the microscope unit 5 is in the direction of gravitational force (the vertical direction), the angle detected by the first angle-sensor unit 24*a* transitions to the state of 90 degrees (the state in which the capturing direction of the imaging unit 21 is horizontal) with respect to the reference direction to 180 degrees (the state in which the capturing direction of the imaging unit 21 is toward the ceiling). Here, the illumination controller 944 may attenuate the intensity of the illumination light supplied from the light source device 3 in an exponential fashion or may attenuate it in a step-by-step manner or linearly. It is obvious that the illumination controller 944 may control the light source device 3 to stop the illumination light supplied from the light source device 3 so as to turn off the light output by the light output unit 22.

Then, the display controller 945 controls the image processing unit 91 to superimpose the information indicating that the observation device 2 is adjusting the light output on the display image on the display device 8, thereby making a notification (Step S109). Thus, according to the first embodiment, the display controller 945 and the display device 8 function as a notifying unit. Furthermore, the display controller 945 may cause an output unit (not illustrated) to output the information indicating that the observation device 2 is adjusting the light output by using sound or light.

Then, when the input unit 92 has received input of termination of the observation by the medical observation system 1 (Step S110: Yes), the medical observation system 1 terminates this process. Conversely, when the input unit 92 has not received input of termination of the observation by the medical observation system 1 (Step S110: No), the medical observation system 1 returns to the above-described Step S101.

At Step S111, the illumination controller 944 controls the intensity of the illumination light supplied from the light source device 3 in accordance with the operation received by the input unit 25, thereby adjusting the light output that is output by the light output unit 22. In this case, priority is given to the user's operation even when the adjustment function mode is set in the observation device 2. For example, there may be also a case where the imaging unit 21 needs to suddenly conduct capturing in an upward direction depending on a surgery even though the user has set the adjustment function mode in the observation device 2 while in use, and therefore the illumination controller 944 gives priority to the user's operation and controls the intensity of the illumination light supplied from the light source device 3 in accordance with the operation received by the input unit 25, thereby adjusting the light output that is output by the light output unit 22. After Step S111, the medical observation system 1 proceeds to Step S110.

At Step S112, the illumination controller 944 terminates the adjustment on the light output that is output by the light output unit 22. Specifically, the illumination controller 944 returns the intensity of the illumination light supplied from the light source device 3 to the intensity in the initial state, thereby terminating the adjustment on the light output that is output by the light output unit 22.

Then, the display controller 945 controls the image processing unit 91 so as to stop the information indicating that the observation device 2 is adjusting the light output (Step S113). After Step S113, the medical observation system 1 proceeds to Step S110.

At Step S101, when the input unit 92 has not received input of a turn-on operation for giving a command to the light source device 3 so as to be turned on (Step S101: No), the medical observation system 1 proceeds to Step S114 described later.

Then, when the input unit 92 has received input of a turn-off operation for giving a command to the light source device 3 so as to be turned off (Step S114: Yes), the illumination controller 944 stops the light source device 3 (Step S115). Thus, the light source device 3 may stop the illumination light supplied to the observation device 2. Furthermore, in this case, the illumination controller 944 does not need to completely stop the light source device 3 but it may set the intensity of the illumination light to the lowest value so as to enable an immediate recovery. After Step S115, the medical observation system 1 proceeds to Step S103.

At Step S114, when the input unit 92 has not received input of a turn-off operation for giving a command to the light source device 3 so as to be turned off (Step S114: No), the medical observation system 1 proceeds to Step S103.

According to the above-described first embodiment, the illumination controller 944 controls the illumination light emitted by the light output unit 22 based on a determination result of the determining unit 942, whereby the emission of the illumination light in an unnecessary direction may be prevented without performing a specially added operation, and the possibility of direct visual contact with the illumination light may be easily reduced.

Furthermore, according to the first embodiment, the determining unit 942 determines whether the angle formed between the capturing direction of the imaging unit 21 and the previously set reference direction falls outside the predetermined range and, when the determining unit 942 determines that it falls outside the predetermined range, the illumination controller 944 controls the illumination light output by the light output unit 22 so as to be turned off or reduced, whereby the emission of the illumination light in an unnecessary direction may be avoided without performing a specially added operation, and the illumination light may be prevented from being improperly emitted to the surrounding people other than the user.

Furthermore, according to the first embodiment, when the first-mode setting unit 943 has set the all-free mode in the observation device 2, the illumination controller 944 performs control to turn off or reduce the illumination light emitted by the light output unit 22 and, when the first-mode setting unit 943 has set the electric visual-field move mode (the pivot operation mode or the XY operation mode) in the observation device 2, the illumination controller 944 does not perform control to turn off or reduce the illumination light emitted by the light output unit 22; thus, the illumination light may be maintained during the electric visual-field move mode in which treatment needs to be continued, and only when the capturing direction of the imaging unit 21 is largely changed while treatment is interrupted, the emission of the illumination light in an unnecessary direction may be prevented without performing a specially added operation.

Furthermore, according to the first embodiment, when the second-mode setting unit 946 has set the automatic adjustment mode in the observation device 2, the illumination controller 944 performs the control to turn off or reduce the illumination light emitted by the light output unit 22, whereby it may be optionally selected whether the user uses the function for the control performed by the illumination controller 944 to turn off or reduce the illumination light emitted by the light output unit 22.

Furthermore, according to the first embodiment, when the input unit 25 receives input of an operation to change the intensity of the illumination light emitted by the light output unit 22 in a case where the determining unit 942 determines falling outside the predetermined range, the illumination controller 944 performs control to change the intensity of the illumination light emitted by the light output unit 22 in accordance with the operation, whereby the illumination light may be controlled with priority given to the user's operation.

Furthermore, according to the first embodiment, when the input unit 92 receives input of a command to stop the light source device 3, the illumination controller 944 stops the illumination light supplied to the light source device 3, whereby the emission of the illumination light in an unnecessary direction may be prevented after treatment on the patient is terminated.

Furthermore, although the determining unit 942 determines whether the capturing direction of the imaging unit 21 falls outside the adjustment range based on the angle formed between the reference direction and the detection angle detected by each of the first angle-sensor unit 24a to the sixth angle-sensor unit 24f according to the first embodiment, the microscope unit 5 may be provided with, for example, a tilt sensor so that it is determined whether the observation direction of the imaging unit 21 falls outside the adjustment range based on the angle formed between the reference direction and the detection angle of the tilt sensor. It is obvious that the adjustment range may be optionally changed to a range of more than horizontal.

Furthermore, although the determining unit 942 determines whether the observation direction of the imaging unit 21 falls outside the adjustment range based on the reference direction and the detection angle detected by each of the first angle-sensor unit 24a to the sixth angle-sensor unit 24f according to the first embodiment, it may be determined whether, for example, the distance between the observed object and the imaging unit 21 falls outside the adjustment range (more than a predetermined value). In this case, the imaging unit 21 may be provided with a 3D distance measuring unit including two optical systems (stereo optical systems) having an optical axis parallel to each other and imaging elements in the respective two optical systems so that the determining unit 942 determines whether the distance between the observed object and the imaging unit 21 is more than a predetermined value based on the distance between the observed object and the imaging unit 21, calculated based on the disparity of the observed object contained in imaging signals generated by the two imaging elements included in the 3D distance measuring unit. It is obvious that a distance measurement sensor (phase-difference pixel) capable of detecting a distance may be provided in an imaging element of the imaging unit 21 so that, based on the distance detected by the distance sensor, the determining unit 942 determines whether the distance (the distance due to distance measurement) between the observed object and the imaging unit 21 is more than a predetermined value. Furthermore, the microscope unit 5 may be provided with a laser distance measuring unit that emits laser light, or the like, so that the determining unit 942 determines whether the distance between the observed object and the imaging unit 21 is more than a predetermined value in accordance with the distance based on a distance measurement result of the laser distance measuring unit.

Furthermore, according to the first embodiment, it may be determined whether the distance between the observed object and the imaging unit 21 is less than a predetermined value. In this case, the imaging unit 21 may be provided with a 3D distance measuring unit including two optical systems (stereo optical systems) having an optical axis parallel to each other and imaging elements in the respective two optical systems so that it is determined whether the distance between the observed object and the imaging unit 21, calculated based on the disparity of the observed object contained in imaging signals generated by the two imaging elements included in the 3D distance measuring unit, is less than a predetermined value. It is obvious that a distance measurement sensor (phase-difference pixel) capable of detecting a distance may be provided in an imaging element of the imaging unit 21 so that, based on the distance detected by the distance sensor, the determining unit 942 determines whether the distance between the observed object and the imaging unit 21 is less than a predetermined value. Furthermore, the microscope unit 5 may be provided with a laser distance measuring unit that emits laser light, or the like, so that the determining unit 942 determines whether the distance between the observed object and the imaging unit 21 is less than a predetermined value in accordance with the distance based on a distance measurement result of the laser distance measuring unit.

Furthermore, according to the first embodiment, the medical observation system 1 and a navigation device may be combined. The navigation device includes: a storage unit that stores image data on a patient, captured by an image diagnostic apparatus, such as CT or MRI, with regard to the patient before a surgery; transmitters such as magnetic coils that generate an alternating-current magnetic field with multiple (e.g., several dozens of) currents at a predetermined interval in the microscope unit 5 or in the neighborhood thereof; a receiver that receives at least one of the focus position and the zoom magnification of the medical observation system 1 from the medical observation system 1; and a calculating unit that estimates the position and the observation direction of the microscope unit 5 based on the positional information on each of the transmitters of the microscope unit 5 by detecting the magnetic field generated by the transmitter of the microscope unit 5 via an antenna, or the like, and detecting the positional information on each of the transmitters and that estimates the observation position and the angle of view of the microscope unit 5 based on the focus position and the zoom magnification received from the medical observation system 1. The navigation device displays the site observed by the medical observation system 1 on an image of the patient based on a calculation result and image data on the patient, stored in the storage unit. Therefore, the determining unit 942 may determine whether the observation direction of the imaging unit 21 falls outside the adjustment range based on the capturing direction of the imaging unit 21 detected by the navigation device and the angle of the capturing direction with respect to the reference direction (the direction of gravitational force). It is obvious that the function of the determining unit 942 may be provided in the navigation device and a determination result may be output to the control device 9. Furthermore, the navigation position detection may be by, instead of a transmitter such as magnetic coil, a reflector and a stereo camera detecting the reflected light from the reflector after projecting the reference light that is invisible light so that the position of the reflector may be calculated.

(Second Embodiment)

Next, a second embodiment is explained. The second embodiment is different from the above-described first embodiment in the configuration of the light source device 3 in the medical observation system 1 and is different in a process performed. Specifically, a light source device according to the second embodiment supplies, as illumination light, white light or special light. Hereafter, the configuration of a medical observation system according to the second embodiment is explained and then a process performed by the medical observation system according to the second embodiment is explained.

[Functional Configuration of the Medical Observation System]

Figure 5:
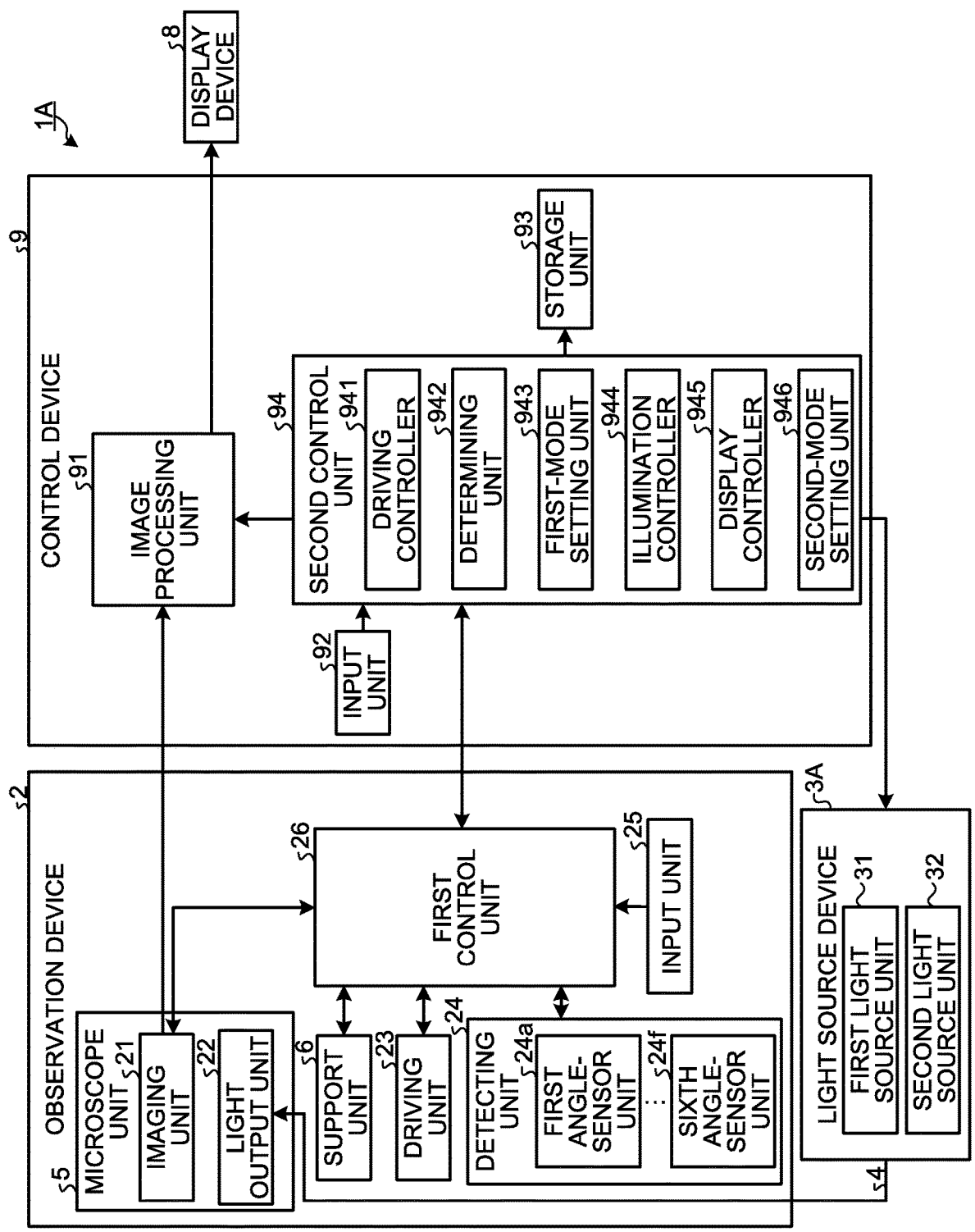
FIG. 5 is a block diagram that illustrates a functional configuration of a medical observation system according to a second embodiment.

FIG. 5 is a block diagram that illustrates a functional configuration of the medical observation system according to the second embodiment. A medical observation system 1A illustrated in FIG. 5 includes a light source device 3A instead of the light source device 3 according to the above-described first embodiment.

The light source device 3A includes: a first light source unit 31 that supplies first illumination light (hereafter, referred to as "white light") having a first wavelength characteristic to the observation device 2; and a second light source unit 32 that supplies second illumination light (hereafter, referred to as "special light") having a second wavelength characteristic different from the first wavelength characteristic to the observation device 2.

The first light source unit 31 supplies white light to the observation device 2 via the light guide 4 under the control of the control device 9. The first light source unit 31 is configured by using a discharge lamp such as xenon lamp or metal halide lamp, a solid light emitting element such as LED or LD, a light emitting member such as a laser light source or a halogen lamp, and the like.

The second light source unit 32 supplies special light to the observation device 2 via the light guide under the control of the control device 9. When the second light source unit 32 is configured by using a discharge lamp such as xenon lamp or metal halide lamp, a filter allowing the passage of a predetermined wavelength band is provided on the optical path of the light guide 4 and the lamp. Furthermore, when the second light source unit 32 is configured by using a solid light emitting element such as LED or LD or a laser light source, light having a predetermined wavelength band is output. Here, the special light includes any one of infrared light (e.g., 790 to 820 nm, 905 to 970 nm), narrow-band light (390 to 445 nm, 530 to 550 nm), excitation light (e.g., blue excitation light (390 to 440 nm)) excited with respect to fluorescence reagent, and the like.

[Process of the Medical Observation System]

Next, a process performed by the medical observation system 1A is explained.

Figure 6:
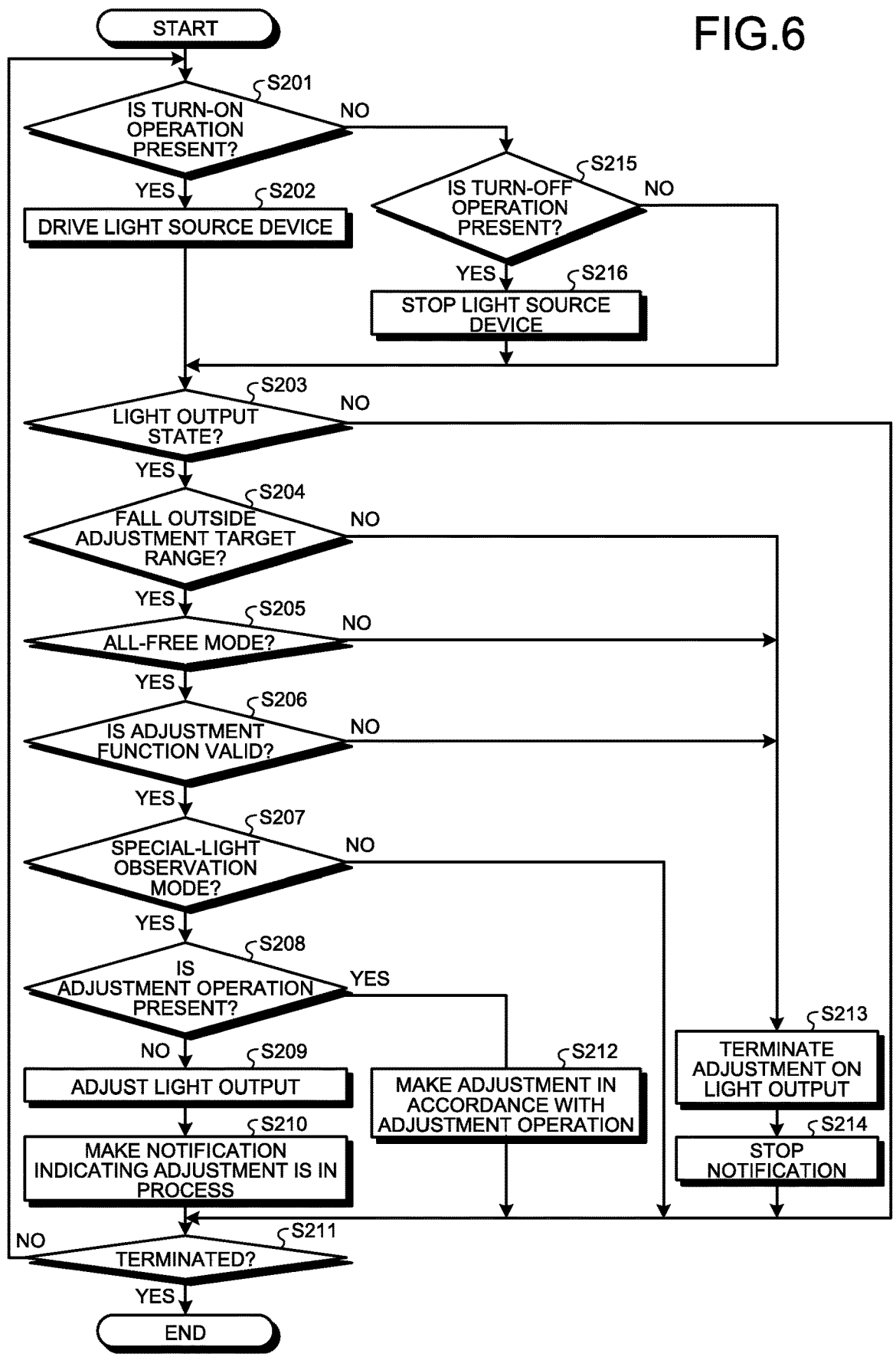
FIG. 6 is a flowchart that illustrates the outline of a process performed by the medical observation system according to the second embodiment.

FIG. 6 is a flowchart that illustrates the outline of the process performed by the medical observation system 1A. In FIG. 6, Step S201 to Step S206 and Step S208 to Step S216 correspond to Step S101 to Step S115, respectively, in the above-described FIG. 4, and therefore explanation is omitted.

At Step S207, the determining unit 942 determines whether the observation device 2 has been set to a special-light observation mode. Specifically, in accordance with an operation on the input unit 92, the determining unit 942 determines whether the first-mode setting unit 943 has set a special-light observation mode in which the light source device 3A supplies the special light and the light output unit 22 outputs the special light. When the determining unit 942 determines that the observation device 2 has been set to the special-light observation mode (Step S207: Yes), the medical observation system 1A proceeds to Step S208. Conversely, when the determining unit 942 determines that the observation device 2 has not been set to the special-light observation mode (Step S207: No), the medical observation system 1A proceeds to Step S211.

According to the second embodiment described above, the same advantageous effect as that in the above-described first embodiment is produced, and when the determining unit 942 determines falling outside the predetermined range and when the light source device 3A supplies the special light to the light output unit 22 (the first-mode setting unit 943 has set the special-light observation mode in which the light source device 3A supplies the special light and the light output unit 22 outputs the special light), the illumination controller 944 controls the special light so as to be turned off or reduced; thus, the emission of the special light in an unnecessary direction may be prevented.

Furthermore, according to the second embodiment, it is possible to prevent light having a wavelength band of invisible light from being emitted to the surrounding people other than the user.

Furthermore, according to the second embodiment, the light source device 3A is configured by using a single white light source for white light; however, this is not a limitation, and a red (R) light source capable of outputting light (red light) having a red wavelength band, a green (G) light source capable of outputting light (green light) having a green wavelength band, and a blue (B) light source capable of outputting light (blue light) having a blue wavelength band may be provided so that white light is produced by causing the red light source, the green light source, and the blue light source to simultaneously emit light. In this case, the illumination controller 944 turns off or reduces light from the blue light source based on a determination result of the determining unit 942. For example, the illumination controller 944 may control the blue light source to turn off or reduce light when the determining unit 942 determines that the microscope unit 5 falls within the adjustment target range. This allows high-intensity light, such as blue light, to be exclusively turned off or reduced.

Furthermore, according to the second embodiment, when the determining unit 942 determines falling outside the predetermined range and when the light source device 3A supplies the special light to the light output unit 22, the illumination controller 944 controls the special light to be turned off or reduced; however, when the light source device 3A simultaneously supplies two lights, special light (e.g., infrared light, narrow-band light, excitation light, and ultraviolet light) and white light, to the light output unit 22, the illumination controller 944 may control the special light to be exclusively turned off or reduced. It is obvious that, when the light source device 3A simultaneously supplies two lights, special light (e.g., infrared light, narrow-band light, excitation light, and ultraviolet light) and white light, to the light output unit 22, the illumination controller 944 may control the white light to be exclusively turned off or reduced. Furthermore, when the light source device 3A simultaneously supplies two lights, special light (e.g., infrared light, narrow-band light, excitation light, and ultraviolet light) and white light, to the light output unit 22, the illumination controller 944 may control each of the white light and the special light to be turned off or reduced. Thus, it is possible to perform control so as to exclusively turn off or reduce light having a wavelength band that needs to be turned off or reduced.

Furthermore, although the illumination controller 944 controls driving to, for example, turn on, turn off, or reduce the light source device 3A according to the second embodiment, this is not a limitation and, for example, it may control a marker emitting unit that is disposed in the microscope unit 5 and that emits marker light indicating the capturing position of the imaging unit 21 to the observed object. In this case, the illumination controller 944 turns off or reduces the marker light based on a determination result of the determining unit 942. For example, the illumination controller 944 may control the marker emitting unit so as to turn off or reduce the light when the determining unit 942 determines that the microscope unit 5 falls within the adjustment target range. It is obvious that the illumination controller 944 may also perform the same process described above on a distance measuring unit that outputs infrared light, or the like, to measure the distance between the observed object and the microscope unit 5.

(Third Embodiment)

Next, a third embodiment is explained. According to the above-described first embodiment, the present invention is applied to the medical observation system using the surgical microscope that enlarges and captures a predetermined visual field area inside the subject (the inside of a living body) or the surface of the subject (the surface of a living body); however, according to the third embodiment, a medical observation system using a rigid endoscope (insertion unit) insertable into the subject is applied. Moreover, the same component as that in the medical observation system 1 according to the above-described first embodiment is attached with the same reference numeral, and explanation is omitted.

[Schematic Configuration of the Medical Observation System]

Figure 7:
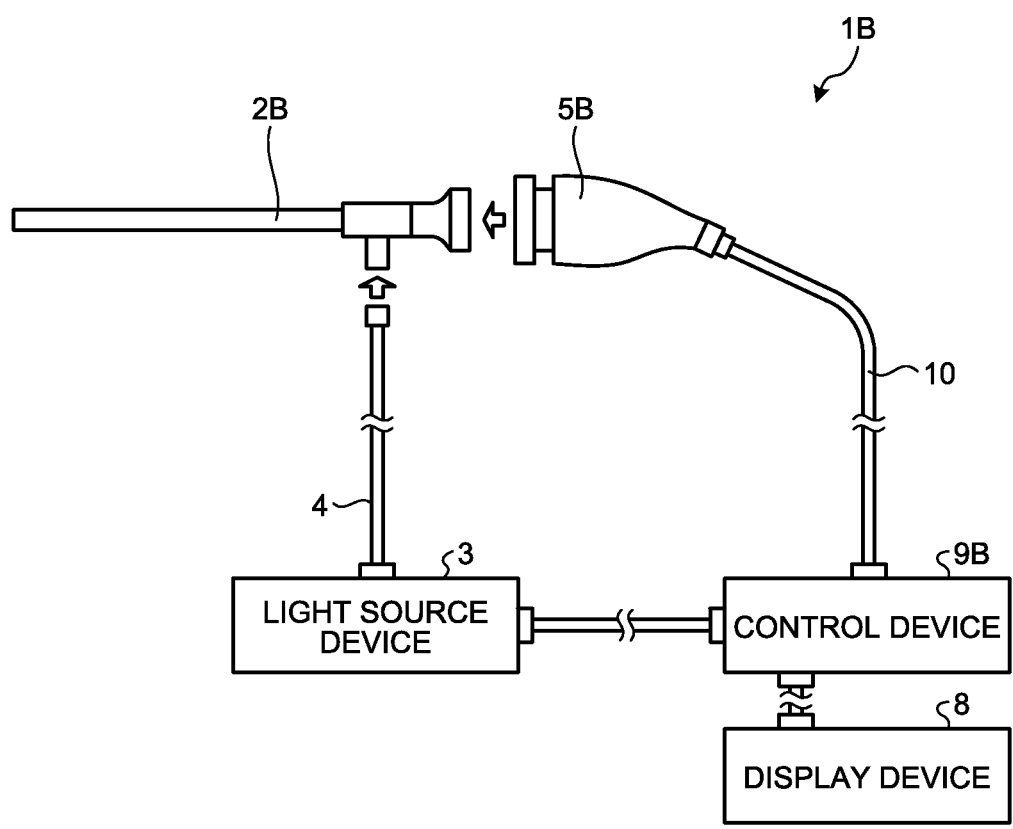
FIG. 7 is a diagram that illustrates a schematic configuration of a medical observation system according to a third embodiment.

FIG. 7 is a diagram that illustrates a schematic configuration of a medical observation system according to the third embodiment. A medical observation system 1B illustrated in FIG. 7 is a system that is used in the medical field for observing the inside of the subject, such as living body. Furthermore, although a rigid endoscope using an observation device (an insertion unit 2B) illustrated in FIG. 1 is explained as the medical observation system 1B according to the third embodiment, this is not a limitation, and it may be a flexible endoscope.

As illustrated in FIG. 7, the medical observation system 1B includes the insertion unit 2B, the light source device 3, the light guide 4, a camera head 5B (imaging device for endoscopy), the display device 8, a control device 9B, and a transmission cable 10.

The insertion unit 2B is rigid or at least partially flexible, has an elongated shape, and is inserted into the subject such as a patient. Inside the insertion unit 2B is provided an optical system that is configured by using one or more lens to form an observation image.

The camera head 5B has the insertion unit 2B connected thereto in an attachable and detachable manner. Under the control of the control device 9B, the camera head 5B captures an observation image formed by the insertion unit 2B and converts its imaging signal (electric signal) into an optical signal and outputs it.

One end of the transmission cable 10 is connected to the control device 9B in an attachable and detachable manner, and the other end is connected to the camera head 5B in an attachable and detachable manner. The transmission cable 10 transmits image signals output from the camera head 5B to the control device 9B and transmits control signals, synchronization signals, clocks, electric power, and the like, output from the control device 9B to the camera head 5B.

[Functional Configuration of the Medical Observation System]

Figure 8:
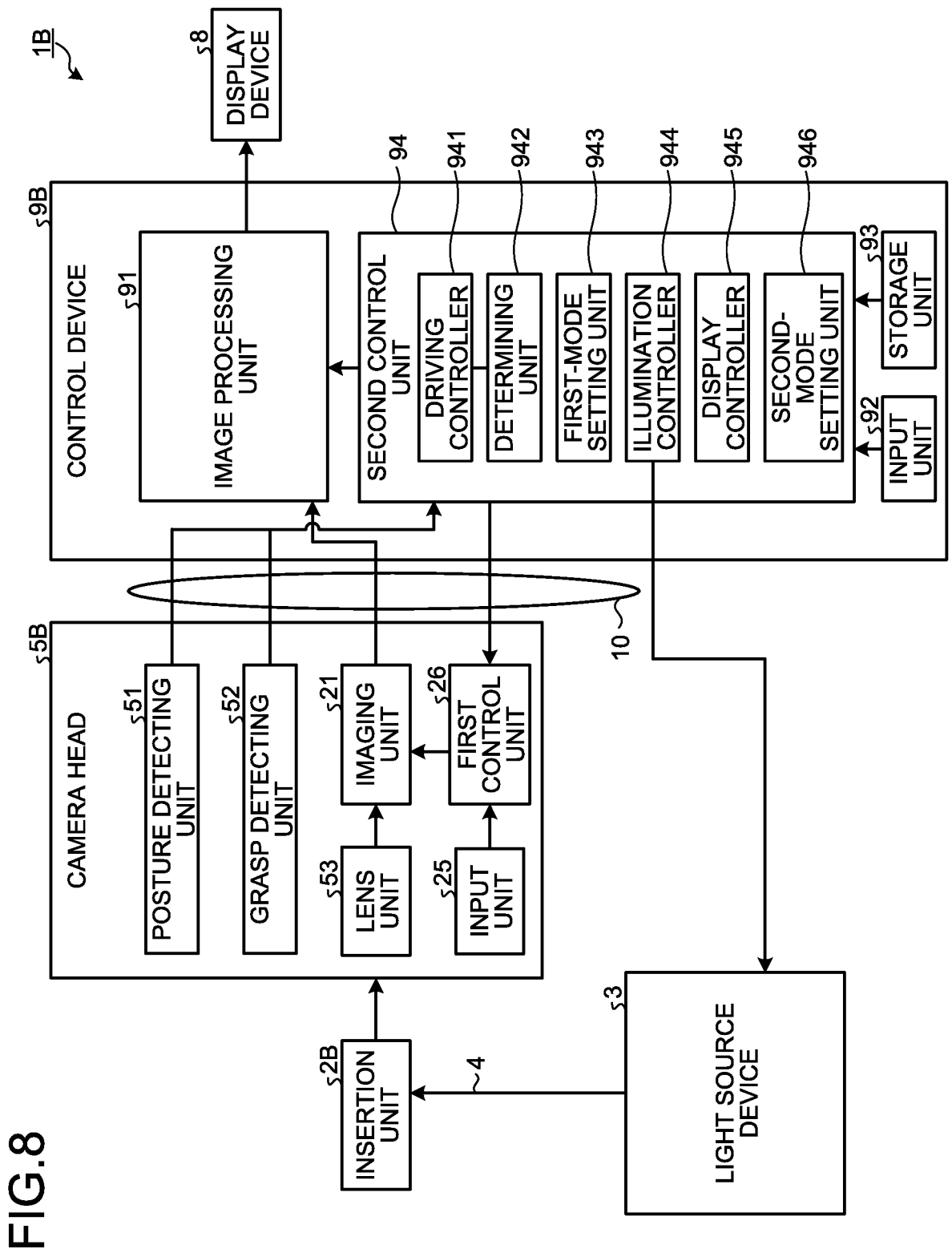
FIG. 8 is a block diagram that illustrates a functional configuration of the medical observation system according to the third embodiment.

Next, a functional configuration of the medical observation system 1B is explained. FIG. 8 is a block diagram that illustrates a functional configuration of the medical observation system 1B.

The camera head 5B includes a posture detecting unit 51, a grasp detecting unit 52, a lens unit 53, the imaging unit 21, the input unit 25, and the first control unit 26.

The posture detecting unit 51 detects the posture state of the camera head 5B and outputs the detection result to the control device 9B. Specifically, the posture detecting unit 51 detects the posture state of the camera head 5B including the insertion unit 2B in a state where the insertion unit 2B is connected to the camera head 5B. For example, the posture detecting unit 51 detects the angle of the camera head 5B with respect to the reference direction in a state where the insertion unit 2B is connected to the camera head 5B and outputs the detected angle to the control device 9B. Here, the reference direction is downward in the direction of gravitational force (the vertical direction).

The grasp detecting unit 52 detects whether the user is grasping the camera head 5B and outputs the detection result to the control device 9B. The grasp detecting unit 52 is configured by using a pressing-force sensor, a pressure sensor, a thermal sensor, or the like, and it is disposed on the outer surface of the camera head 5B, on which the user grasps the camera head 5B.

The lens unit 53 is configured by using one or more lenses, and it forms an object image focused by the insertion unit 2B on the imaging surface of an imaging element (not illustrated) included in the imaging unit 21. The one or more lenses are configured to be movable along the optical axis. Furthermore, the lens unit 53 has at least the focus mechanism for changing the focus position and the zoom mechanism for changing the angle of view by moving the one or more lenses. Moreover, the lens unit 53 may be provided with a diaphragm mechanism and an optical filter (e.g., a filter that cuts infrared light) that is attachable and detachable on the optical axis.

[Process of the Medical Observation System]

Figure 9:
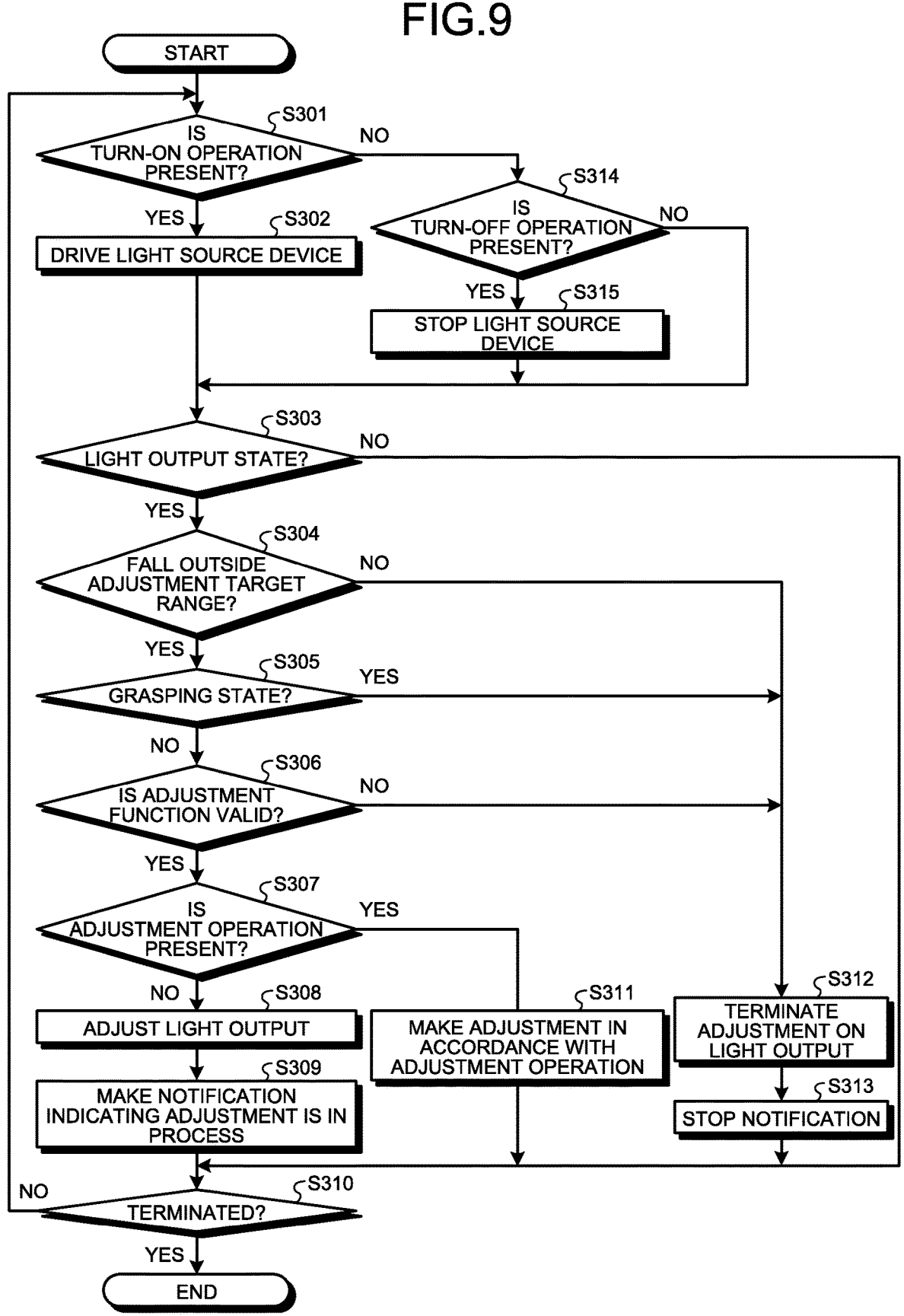
FIG. 9 is a flowchart that illustrates the outline of a process performed by the medical observation system according to the third embodiment.

Next, a process performed by the medical observation system 1B is explained. FIG. 9 is a flowchart that illustrates the outline of the process performed by the medical observation system 1B. In FIG. 9, Step S301 to Step S303 and Step S306 to Step S315 correspond to Step S101 to Step S103 and Step S106 to Step S115, respectively, in the above-described FIG. 4, and therefore detailed explanations are omitted.

At Step S304, the determining unit 942 determines whether the posture state of the camera head 5B, including the insertion unit 2B, detected by the posture detecting unit 51 falls outside the adjustment target range. Specifically, the determining unit 942 determines whether the angle of the camera head 5B including the insertion unit 2B in the capturing direction (the optical-axis direction) with respect to the reference direction, detected by the posture detecting unit 51, falls outside the adjustment target range. For example, the determining unit 942 determines whether the angle of the camera head 5B including the insertion unit 2B in the capturing direction (the optical-axis direction) detected by the posture detecting unit 51 is equal to or more than 90 degrees with respect to the reference direction. That is, the determining unit 942 determines whether the capturing direction of the camera head 5B including the insertion unit 2B is more than horizontal. When the determining unit 942 determines that the posture state of the camera head 5B including the insertion unit 2B detected by the posture detecting unit 51 falls outside the adjustment target range (Step S304: Yes), the medical observation system 1B proceeds to Step S305 described later. Conversely, when the determining unit 942 determines that the posture state of the camera head 5B including the insertion unit 2B, detected by the posture detecting unit 51, does not fall outside the adjustment target range (Step S304: No), the medical observation system 1B proceeds to Step S312.

At Step S305, the determining unit 942 determines whether it is a grasping state in which the user is grasping the camera head 5B based on a detection result detected by the grasp detecting unit 52. When the determining unit 942 determines that it is a grasping state in which the user is grasping the camera head 5B (Step S305: Yes), the medical observation system 1B proceeds to Step S312. Conversely, when the determining unit 942 determines that it is not a grasping state in which the user is grasping the camera head 5B (Step S305: No), the medical observation system 1B proceeds to Step S306.

According to the third embodiment described above, the illumination controller 944 controls the illumination light emitted by the light output unit 22 based on a determination result of the determining unit 942 so as to prevent the emission of the illumination light in an unnecessary direction; thus, even when the medical observation apparatus does not include the above-described observation device 2 (support device), the possibility of direct visual contact with the illumination light may be easily reduced without performing a specially added operation.

Furthermore, according to the third embodiment, the medical observation system 1B and a navigation device may be combined. The navigation device includes: a storage unit that stores image data on a patient, captured by an image diagnostic apparatus, such as CT or MRI, with regard to the patient before a surgery; transmitters such as magnetic coils that generate an alternating-current magnetic field with multiple (e.g., several dozens of) currents at a predetermined interval in the entire length at the distal end part along the longitudinal direction of the insertion unit 2B; and a calculating unit that estimates the insertion length, the focus position, and the observation direction of the insertion unit 2B based on the positional information on each of the transmitters of the insertion unit 2B by detecting the magnetic field generated by the transmitter of the insertion unit 2B via an antenna, or the like, and detecting the positional information on each of the transmitters. The navigation device displays the site observed by the medical observation system 1B on an image of the patient based on a calculation result and image data on the patient, stored in the storage unit. Therefore, the determining unit 942 may determine whether the observation direction of the imaging unit 21 falls outside the adjustment range based on the capturing direction of the imaging unit 21 detected by the navigation device and the angle of the capturing direction with respect to the reference direction (the direction of gravitational force). It is obvious that the function of the determining unit 942 may be provided in the navigation device and a determination result may be output to the control device 9. Furthermore, the navigation position detection may be by, instead of a transmitter such as magnetic coil, a reflector and a stereo camera detecting the reflected light from the reflector after projecting the reference light that is invisible light so that the position of the reflector may be calculated. This allows implementation without posture detection by the medical observation system.

(Fourth Embodiment)

Next, a fourth embodiment is explained. The fourth embodiment is different from the above-described first embodiment in the configuration of the control device 9 in the medical observation system 1 and is different in a process performed. Specifically, a medical observation system according to the fourth embodiment detects a predetermined image pattern, which is previously set, from an image that corresponds to an image signal and controls the illumination light, output by the light output unit, so as to be turned off or reduced in accordance with a detection result. Hereafter, the configuration of the medical observation system according to the fourth embodiment is explained, and then a process performed by the medical observation system according to the fourth embodiment is explained. Moreover, the same component as that in the medical observation system 1 according to the above-described first embodiment is attached with the same reference numeral, and explanation is omitted.

[Functional Configuration of the Medical Observation System]

Figure 10:
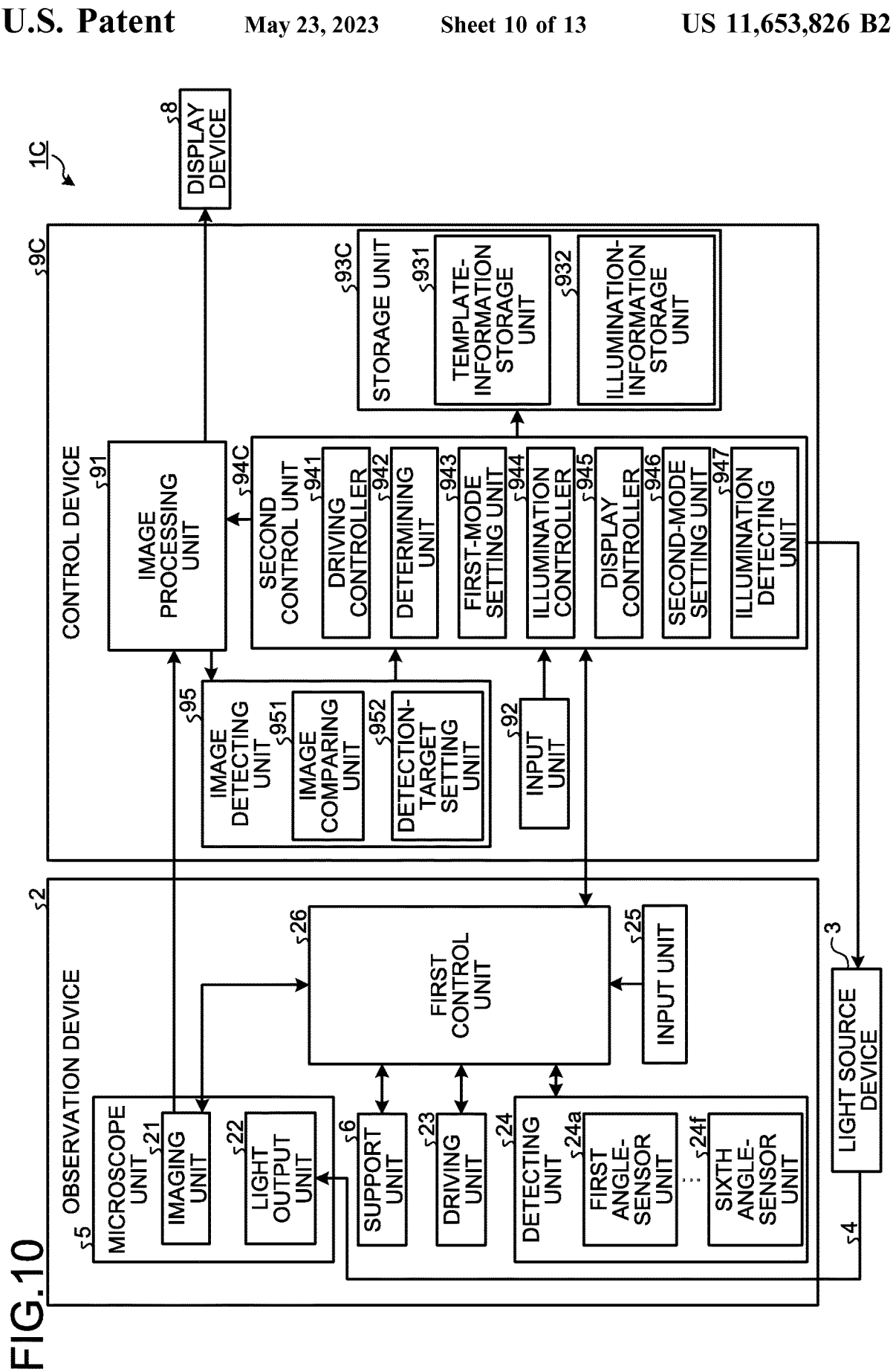
FIG. 10 is a block diagram that illustrates a functional configuration of a medical observation system according to a fourth embodiment.

FIG. 10 is a block diagram that illustrates a functional configuration of the medical observation system according to the fourth embodiment. A medical observation system 1C illustrated in FIG. 10 includes a control device 9C instead of the control device 9 according to the above-described first embodiment.

The control device 9C includes a storage unit 93C and a second control unit 94C instead of the storage unit 93 and the second control unit 94 of the control device 9 according to the above-described first embodiment. Furthermore, the control device 9C further includes an image detecting unit 95.

The storage unit 93C is configured by using a semiconductor memory, such as flash memory or DRAM, and it temporarily stores various programs executed by the medical observation system 1C and data in processing. Furthermore, the storage unit 93C includes: a template-information storage unit 931 that stores template information for the image detecting unit 95 to detect a predetermined image pattern, which is previously set; and an illumination-information storage unit 932 that stores illumination information, detected by an illumination detecting unit 947 described later, regarding the illumination state of the illumination light output by the light output unit 22. Here, the template information is a template, feature data, and a learning machine regarding a person's face, eye, and internal organ. Furthermore, the template information may include feature data and templates regarding treatment tools such as forceps or scalpel, blood, water, and the like. Here, the feature data is a luminance value, a color, a shape, and the like.

The second control unit 94C further includes the illumination detecting unit 947 in addition to the configuration of the second control unit 94 according to the above-described first embodiment.

The illumination detecting unit 947 detects illumination information regarding the illumination state of the illumination light output by the light output unit 22.

The image detecting unit 95 detects a predetermined image pattern, which is previously set, from an image corresponding to the image signal generated by the imaging unit 21 and outputs the detection result to the determining unit 942. The image detecting unit 95 includes an image comparing unit 951 and a detection-target setting unit 952.

The image comparing unit 951 compares the image corresponding to the image signal generated by the imaging unit 21 with the detection target or the detection condition set by the detection-target setting unit 952 described later by using pattern matching, thereby detecting the detection target or the detection condition from the image corresponding to the image signal.

The detection-target setting unit 952 sets the detection target or the detection condition that is detected by the image comparing unit 951 from the image corresponding to the image signal generated by the imaging unit 21. Specifically, the detection-target setting unit 952 acquires template information corresponding to the detection target or the detection condition selected by the input unit 92 from the template-information storage unit 931 and sets the acquired template information in the image comparing unit 951. For example, the detection-target setting unit 952 sets the detection of a face or eye in the image comparing unit 951.

[Process of the Medical Observation System]

Next, a process of the medical observation system 1C is explained.

Figure 11:
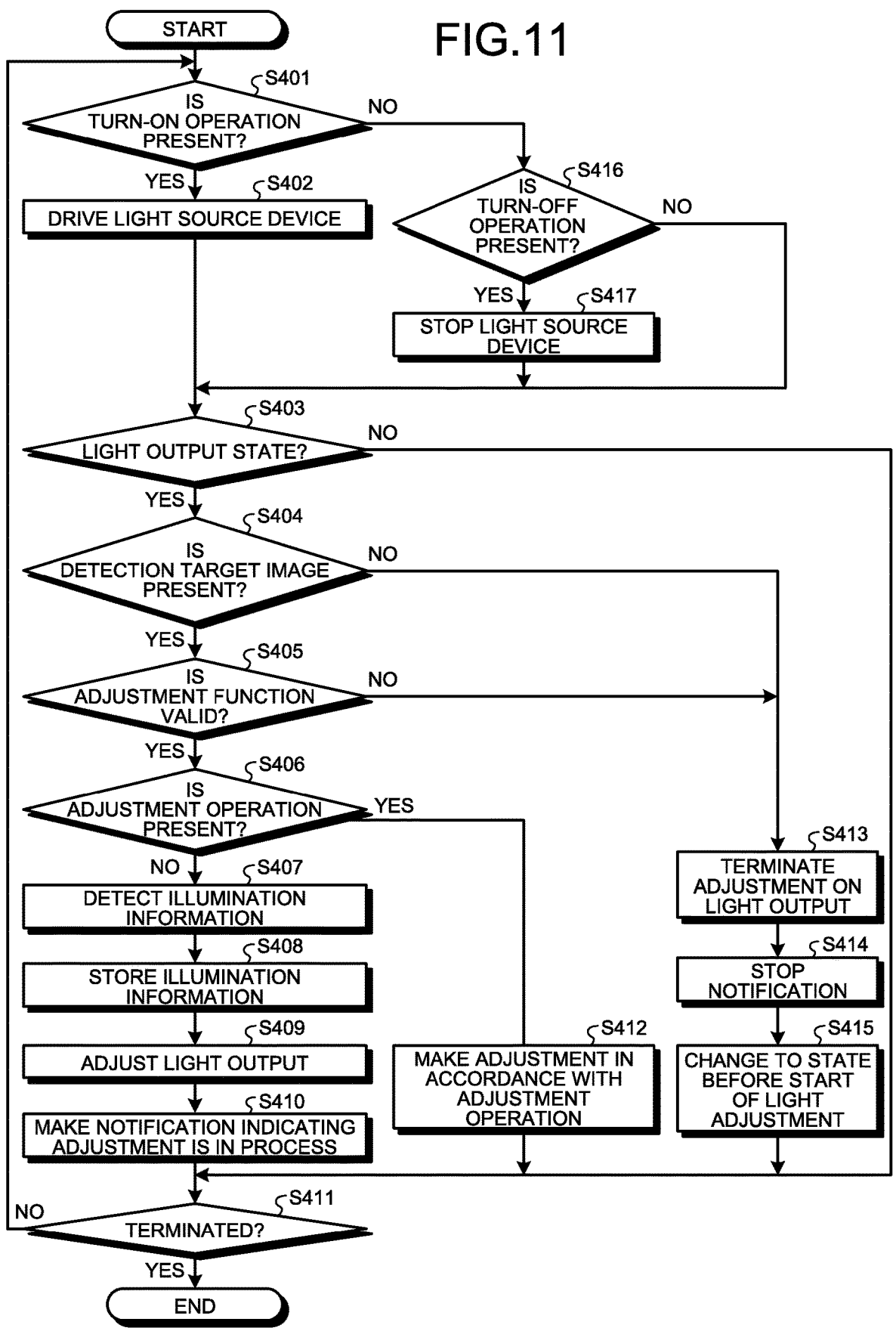
FIG. 11 is a flowchart that illustrates the outline of a process performed by the medical observation system according to the fourth embodiment.

FIG. 11 is a flowchart that illustrates the outline of the process performed by the medical observation system 1C. Step S401 to Step S403 correspond to Step S101 to Step S103, respectively, in the above-described FIG. 4.

At Step S404, the determining unit 942 determines whether the image detecting unit 95 has detected the detection target from the image corresponding to the image signal generated by the imaging unit 21. When the determining unit 942 determines that the image detecting unit 95 has detected the detection target from the image corresponding to the image signal generated by the imaging unit 21 (Step S404: Yes), the medical observation system 1C proceeds to Step S405 described later. Conversely, when the determining unit 942 determines that the image detecting unit 95 has not detected the detection target from the image corresponding to the image signal generated by the imaging unit 21 (Step S404: No), the medical observation system 1C proceeds to Step S413 described later.

Step S405 and Step S406 correspond to Step S106 and Step S107, respectively, in the above-described FIG. 4.

At Step S407, the illumination detecting unit 947 detects illumination information regarding the illumination state of the illumination light output by the light output unit 22.

Then, the illumination controller 944 stores the illumination information previously detected by the illumination detecting unit 947 in the illumination-information storage unit 932 (Step S408). After Step S408, the medical observation system 1C proceeds to Step S409 described later.

Step S409 to Step S414 correspond to Step S108 to Step S113, respectively, in the above-described FIG. 4.

At Step S415, before canceling the control to reduce or turn off the illumination light output by the light output unit 22, the illumination controller 944 performs control to change the illumination state of the illumination light output by the light output unit 22 to the state before the start of the adjustment based on illumination information stored in the illumination-information storage unit 932. Thus, it is possible to instantly make a return to the state before the illumination light output by the light output unit 22 is reduced or turned off. After Step S415, the medical observation system 1C proceeds to Step S411.

Step S416 and Step S417 correspond to Step S114 and Step S115, respectively, in the above-described FIG. 4.

According to the fourth embodiment described above, the illumination controller 944 controls the illumination light emitted by the light output unit 22 when the determining unit 942 determines that the image detecting unit 95 has detected the detection target, whereby the emission of the illumination light in an unnecessary direction may be prevented without performing a specially added operation and, even when there is no holding member that holds the microscope unit 5, the possibility of direct visual contact with the illumination light may be easily reduced.

Furthermore, according to the fourth embodiment, before canceling the control to reduce or turn off the illumination light output by the light output unit 22, the illumination controller 944 performs control to change the illumination state of the illumination light output by the light output unit 22 to the state before the start of light adjustment based on illumination information stored in the illumination-information storage unit 932. Thus, it is possible to instantly make a return to the state before the illumination light output by the light output unit 22 is reduced or turned off, and it is possible to automatically switch the operating state and the light-off state or and the light reduced state.

Furthermore, although the image detecting unit 95 detects a person's eye or face from an image by template matching according to the fourth embodiment, a specific organ (e.g., liver or stomach) may be detected from an image by using known template matching.

Furthermore, although the image detecting unit 95 detects a person's eye or face from an image by template matching according to the fourth embodiment, a treatment tool, such as forceps or scalpel, may be detected from an image by using known template matching (e.g., the shape of forceps).

Furthermore, although the image detecting unit 95 detects a person's eye or face from an image by template matching according to the fourth embodiment, the size of blood, water, or the like, occupied in an image may be detected. In this case, the image detecting unit 95 detects that blood or water is included when the luminance value of the entire image is more than a predetermined value. It is obvious that the image detecting unit 95 may detect that, when the percentage of a predetermined color component, other than a luminance value, for example in the case of blood, a red color component occupied in the entire image is more than a predetermined value, blood is included. This makes it possible to reduce or turn off the light in the case of regular reflection of the illumination light.

Furthermore, although the illumination controller 944 performs control to change the illumination state of the illumination light output by the light output unit 22 to the state before the end of the adjustment based on illumination information stored in the illumination-information storage unit 932 before canceling the control to reduce or turn off the illumination light output by the light output unit 22 according to the fourth embodiment, this is not a limitation; for example, when the control to reduce or turn off the illumination light output by the light output unit 22 is canceled, the illumination controller 944 may gradually increase the illumination state of the illumination light output by the light output unit 22 from the lowest intensity state of the illumination light output by the light output unit 22 to the intensity state before the end of the adjustment. Thus, the rapid output of the strong illumination light may be prevented when the light-off state or the light reduced state is automatically canceled.

Furthermore, the illumination controller 944 may perform the control such that the illumination light, output by the light output unit 22, is emitted with the lowest value of the light intensity before canceling the control to reduce or turn off the illumination light output by the light output unit 22 according to the fourth embodiment. Thus, the rapid output of the strong illumination light may be prevented when the light-off state or the light reduced state is automatically canceled.

(Fifth Embodiment)

Next, a fifth embodiment is explained. The fifth embodiment is different from the above-described first embodiment in the configuration of the observation device 2 and the control device 9 in the medical observation system 1 and is different in a process performed. Specifically, the medical observation system according to the fifth embodiment switches the function of turning off the light or reducing the light to be enabled or disabled in accordance with the type of observation unit including an imaging unit and a light output unit. Hereafter, a configuration of a medical observation system according to the fifth embodiment is explained and then a process performed by the medical observation system according to the fifth embodiment is explained. Moreover, the same component as that in the medical observation system 1 according to the above-described first embodiment is attached with the same reference numeral, and explanation is omitted.

[Functional Configuration of the Medical Observation System]

FIG. 12 is a block diagram that illustrates a functional configuration of the medical observation system according to the fifth embodiment. A medical observation system 1D illustrated in FIG. 12 includes an observation device 2D and a control device 9D instead of the observation device 2 and the control device 9 according to the above-described first embodiment.

[Configuration of the Observation Device]

First, a functional configuration of the observation device 2D is explained.

The observation device 2D includes an observation unit 5D and a first control unit 26D instead of the microscope unit 5 and the first control unit 26 according to the above-described first embodiment. Furthermore, the observation device 2D further includes a holding unit 27. The holding unit 27 holds the observation unit 5D in an attachable and detachable manner.

The observation unit 5D includes the imaging unit 21, the light output unit 22, and a type-ID storage unit 28. The observation unit 5D is mounted on the holding unit 27 in an attachable and detachable manner.

The type-ID storage unit 28 is configured by using a ROM, and it stores ID information indicating the type of an observation unit.

The first control unit 26D controls operations of the imaging unit 21 and the driving unit 23 in accordance with the input of an operation command received by the input unit 25 and an operation command input from the control device 9D described later. Furthermore, the first control unit 26D is configured by using a CPU, an ASIC, or the like, and it controls the observation device 2D in an integrated manner in cooperation with a second control unit 94D of the control device 9D described later. Furthermore, the first control unit 26D includes a type detecting unit 261.

The type detecting unit 261 detects the ID information on the observation unit 5D from the type-ID storage unit 28 of the observation unit 5D via the holding unit 27 and outputs the detection result to the control device 9D.

[Configuration of the Control Device]

Next, a functional configuration of the control device 9D is explained.

The control device 9D includes a storage unit 93D and a second control unit 94D instead of the storage unit 93 and the second control unit 94 of the control device 9 according to the above-described first embodiment. Furthermore, the control device 9D further includes the image detecting unit 95 according to the above-described fourth embodiment.

The storage unit 93D is configured by using a semiconductor memory such as flash memory or DRAM, and it temporarily stores various programs executed by the medical observation system 1D and data in processing. The storage unit 93D further includes an illumination-parameter storage unit 933 in addition to the template-information storage unit 931 and the illumination-information storage unit 932 according to the above-described fourth embodiment. The illumination-parameter storage unit 933 stores illumination-parameter setting information about each of illumination operation modes in which there are different illumination parameters including the light intensity, the illumination range, and flashing/non-flashing of the illumination light output by the light output unit 22.

The second control unit 94D controls each unit of the medical observation system 1D in an integrated manner. The second control unit 94D is implemented by using a general-purpose processor such as a CPU having an internal memory (not illustrated) with a program stored therein, or a dedicated processor such as various arithmetic circuits performing a specific function, e.g., ASIC. Furthermore, it may be configured by using an FPGA that is one type of programmable integrated circuit. Moreover, when it is configured by using an FPGA, a memory that stores configuration data may be provided, and an FPGA, which is a programmable integrated circuit, may be configured with configuration data that is read from the memory. The second control unit 94D further includes an illumination-operation setting unit 948, a mode detecting unit 949, and a determination controller 950 in addition to the configuration of the second control unit 94C according to the above-described fourth embodiment.

The illumination-operation setting unit 948 sets, in the light output unit 22, any of the illumination modes in which there are different illumination parameters including the intensity, the illumination range, and flashing/non-flashing of the illumination light output by the light output unit 22. Specifically, the illumination-operation setting unit 948 acquires, from the illumination-parameter storage unit 933, the illumination parameter that corresponds to the illumination mode selected in accordance with a command signal input from the input unit 92 and sets the acquired illumination parameter in the light source device 3 to set the illumination mode in the light output unit 22.

The mode detecting unit 949 detects the illumination mode set in the light output unit 22 by the illumination-operation setting unit 948.

The determination controller 950 switches the determination function of the determining unit 942 so as to be enabled or disabled based on a detection result of the mode detecting unit 949.

[Process of the Medical Observation System]

Next, a process of the medical observation system 1D is explained.

FIG. 13 is a flowchart that illustrates the outline of the process performed by the medical observation system 1D. Step S501 to Step S503 correspond to Step S101 to Step S103, respectively, in the above-described FIG. 4. Step S504 corresponds to Step S404 in the above-described FIG. 11. Step S505 corresponds to Step S106 in the above-described FIG. 4.

At Step S506, the determining unit 942 determines whether the illumination mode detected by the mode detecting unit 949 is the adjustment target. When the determining unit 942 determines that the illumination mode detected by the mode detecting unit 949 is the adjustment target (Step S506: Yes), the medical observation system 1D proceeds to Step S507 described later. Conversely, when it is determined that the illumination mode detected by the mode detecting unit 949 is not the adjustment target (Step S506: No), the medical observation system 1D proceeds to Step S514 described later.

Step S507 to Step S518 correspond to Step S406 to Step S417, respectively, in the above-described FIG. 11.

According to the fifth embodiment described above, when the determining unit 942 determines that the illumination mode detected by the mode detecting unit 949 is the adjustment target, the illumination controller 944 controls the illumination light emitted by the light output unit 22, whereby the emission of the illumination light in an unnecessary direction may be prevented in accordance with the type of the observation unit 5D attached to the holding unit 27 without performing a specially added operation, and the possibility of the direct visual contact with the illumination light may be easily reduced.

Furthermore, according to the fifth embodiment, as the determination controller 950 switches the determination function of the determining unit 942 so as to be enabled or disabled in accordance with a detection result detected by the type detecting unit 261, it is possible to perform control to turn off or reduce the light exclusively for the type of the observation unit 5D required.

Furthermore, according to the fifth embodiment, the determination controller 950 may switch the determination function of the determining unit 942 so as to be enabled or disabled based on the intensity of the illumination mode detected by the mode detecting unit 949, for example, the illumination mode set by the illumination-operation setting unit 948. Thus, it is possible to perform control to turn off or reduce the light exclusively for the intensity of the illumination mode required.

Furthermore, according to the fifth embodiment, the determination controller 950 may switch the determination function of the determining unit 942 so as to be enabled or disabled based on the illumination range of the illumination mode detected by the mode detecting unit 949, for example, the illumination mode set by the illumination-operation setting unit 948. Thus, it is possible to perform control to turn off or reduce the light exclusively for the intensity of the illumination range required.

Furthermore, according to the fifth embodiment, the determination controller 950 may switch the determination function of the determining unit 942 so as to be enabled or disabled based on flashing/non-flashing of the illumination mode detected by the mode detecting unit 949, for example, the illumination mode set by the illumination-operation setting unit 948. Thus, it is possible to perform control to turn off or reduce the light only when the output light is high-intensity flashing light.

Furthermore, although the type detecting unit 261 detects the type of the observation unit 5D and the determination controller 950 switches the determination function of the determining unit 942 so as to be enabled or disabled based on a detection result detected by the type detecting unit 261 according to the fifth embodiment, for example the light guide 4 and the camera head 5B according to the above-described third embodiment may be also used. In this case, the light guide 4 may be provided with the type-ID storage unit 28 or the mark indicating the type of the ride guide 4 depending on its shape, and the type detecting unit 261 disposed in the camera head 5B may detect the type or the mark of the light guide 4. In this case, the determination controller 950 switches the determination function of the determining unit 942 so as to be enabled or disabled based on a detection result detected by the type detecting unit 261. Thus, the illumination light may be controlled in accordance with the type of the light guide 4, and therefore the control to turn off or reduce the light may be performed exclusively for the type of the light guide 4 required.

(Other Embodiments)

Furthermore, although the illumination controller stops the light source device to turn off the light according to the first to the fifth embodiments of the present disclosure, the light may be reduced by decreasing, for example, the drive voltage or the drive current of the light source device. It is obvious that the illumination light supplied to the light source device may be reduced by inserting a filter having different transmissivity on the supply route for supplying the illumination light to the light source device, or light is prevented from being emitted by providing a mirror, or the like.

Furthermore, although the illumination controller controls the illumination light emitted by the light output unit so as to be reduced or turned off based on a determination result of the determining unit according to the first to the fifth embodiments of the present disclosure, for example, the switching control may be performed to gradually make a transition to the light reduced state or the light-off state without performing the control to instantly switch the time in which the illumination light shifts to the light reduced state or the light-off state. This allows a user to intuitively know that a transition has started because of a change in the output illumination light before the light reduced state or the light-off state is fully reached, whereby confusions may be reduced. Furthermore, the user may recover the amount of illumination light as needed before the light reduced state or the light-off state is completely switched.

Furthermore, although the illumination controller instantly performs the control to switch the illumination light emitted by the light output unit so as to be reduced or turned off based on a determination result of the determining unit according to the first to the fifth embodiments of the present disclosure, the illumination controller may start the control to reduce or turn off the illumination light emitted by the light output unit when, for example, the determining unit makes a determination and then the determining unit makes the same determination as the determination result continuously during more than a certain period of time. This prevents a susceptible state in which the light is reduced or turned off due to a momentary duration of a determination result (operation condition) that causes the control to reduce or turn off the light. It is obvious that the time in which the illumination controller starts the control may be set by the input unit, or the like, as appropriate or may be changed as appropriate in accordance with details of a determination.

For explanations of the process by the medical observation system in this description, a sequential order of each step is indicated by using terms such as "first", "next", "then", and "further"; however, the sequential order of a step necessary to implement the present invention is not uniquely defined by using those terms. That is, the order in the medical observation system described in this description may be changed to such a degree that there is no contradiction.

Furthermore, the present invention is not limited to the above-described embodiment as it is, and at the embodiment phase, components may be modified and embodied without departing from the scope of the invention. Further, the components disclosed in the above-described embodiment may be combined as appropriate to form various inventions. For example, some components may be deleted from the entire components described in the above-described embodiment. Furthermore, the components described in each embodiment may be combined as appropriate.

Furthermore, in the description and drawings, if a term is described together with a different term having a broader meaning or the same meaning at least once, it may be replaced with the different term in any part of the description or drawings. Thus, various modifications and applications are possible without departing from the scope of the present invention.

Thus, the present invention may include various embodiments not described here, and various design changes, or the like, may be made within the range of technical ideas specified in claims.

REFERENCE SIGNS LIST 1, 1A, 1B, 1C, 1D MEDICAL OBSERVATION SYSTEM
2, 2D OBSERVATION DEVICE
2B INSERTION UNIT
3, 3A LIGHT SOURCE DEVICE
4 LIGHT GUIDE
5 MICROSCOPE UNIT
5B CAMERA HEAD
6 SUPPORT UNIT
7 BASE UNIT
8 DISPLAY DEVICE
9, 9B, 9C, 9D CONTROL DEVICE
10 TRANSMISSION CABLE
21 IMAGING UNIT
22 LIGHT OUTPUT UNIT
23 DRIVING UNIT
24 DETECTING UNIT
24a to 24f FIRST ANGLE-SENSOR UNIT TO SIXTH ANGLE-SENSOR UNIT
25, 92 INPUT UNIT
26 FIRST CONTROL UNIT
27 HOLDING UNIT
28 TYPE-ID STORAGE UNIT
31 FIRST LIGHT SOURCE UNIT
32 SECOND LIGHT SOURCE UNIT
51 POSTURE DETECTING UNIT
52 GRASP DETECTING UNIT
53 LENS UNIT
61 to 66 FIRST JOINT UNIT TO SIXTH JOINT UNIT
71 to 75 FIRST ARM UNIT TO FIFTH ARM UNIT
91 IMAGE PROCESSING UNIT
93, 93C, 93D STORAGE UNIT
94, 94C, 94D SECOND CONTROL UNIT
95 IMAGE DETECTING UNIT
931 TEMPLATE-INFORMATION STORAGE UNIT
932 ILLUMINATION-INFORMATION STORAGE UNIT
933 ILLUMINATION-PARAMETER STORAGE UNIT
941 DRIVING CONTROLLER
942 DETERMINING UNIT
943 FIRST-MODE SETTING UNIT
944 ILLUMINATION CONTROLLER
945 DISPLAY CONTROLLER
946 SECOND-MODE SETTING UNIT
947 ILLUMINATION DETECTING UNIT
948 ILLUMINATION-OPERATION SETTING UNIT
949 MODE DETECTING UNIT
950 DETERMINATION CONTROLLER
951 IMAGE COMPARING UNIT
952 DETECTION-TARGET SETTING UNIT

The invention claimed is:

1. A medical observation system comprising:
an image sensor configured to capture an object and generates an image signal;
a light source configured to output illumination light in a capturing direction of the image sensor;
a determining circuit configured to determine a usage state of the image sensor;
a support configured to hold the image sensor and the light source and movably support the image sensor and the light source;
a first-mode setting circuit configured to set, in the medical observation system, any one of an electric visual-field move mode, in which a capturing visual field of the image sensor is changeable in upward, downward, leftward, and rightward directions by fixing a part of axes of joints included in the support and moving a different axis in accordance with a command input from outside, and an all-free mode in which the capturing direction of the image sensor is changeable by allowing rotation of the image sensor about the axis of any joint;
a driving control circuit configured to control driving of the support in accordance with a setting of the first-mode setting circuit; and
an illumination control circuit configured to control illumination light emitted by the light source based on the usage state determined by the determining circuit and, on condition that light is being output by the light source and on condition that the first-mode setting circuit has set the all-free mode and the usage state indicates that the image sensor is outside an adjustment target range, control the illumination light emitted by the light source to be turned off or reduced.

2. The medical observation system according to claim 1, further comprising:
a support configured to hold the image sensor and the light source and movably support the image sensor and the light source; and
a detector configured to detect an angle formed between the capturing direction of the image sensor and a previously set reference direction, wherein
the determining circuit is configured to determine that the image sensor is outside the adjustment target range on condition that the angle detected by the detector falls outside a predetermined range.

3. The medical observation system according to claim 1, further comprising:
a camera head including the image sensor disposed at an inner side thereof; and
a detector configured to detect an angle formed between a capturing direction of the image sensor and a previously set reference direction, wherein
the determining circuit is configured to determine whether the angle detected by the detector falls outside a predetermined range, and
when the determining circuit determines that the image sensor is outside the adjustment target range when the angle falls outside the predetermined range, the illumination control circuit is configured to control the illumination light emitted by the light source to be turned off or reduced.

4. The medical observation system according to claim 3, further comprising a grasp detector configured to detect whether the camera head is grasped by a user, wherein
the determining circuit is configured to determine whether the user is grasping the camera head in accordance with a detection result of the grasp detector, and
when the determining circuit determines that the user is not grasping the camera head, the illumination control circuit controls the illumination light emitted by the light source so as to be turned off or reduced, and, on condition that the user is grasping the camera head, not reduce or turn off the illumination light even when the image sensor is outside the adjustment target range.

5. The medical observation system according to claim 1, further comprising a detector configured to detect a distance from an object captured by the image sensor to a distal end part of the image sensor wherein
the determining circuit is configured to determine whether a distance detected by the detector is more than a predetermined value, and when the determining circuit determines that the image sensor is outside the adjustment target range when the distance detected is more than the predetermined value, the illumination control circuit is configured to control the illumination light emitted by the light source to be turned off or reduced.

6. The medical observation system according to claim 1, further comprising a first input configured to receive input of an operation to change an intensity of the illumination light emitted by the light source, wherein
when the first input receives input of the operation in a case where the determining circuit determines the image sensor is outside the adjustment target range, the illumination control circuit performs control to change the intensity of the illumination light emitted by the light source.

7. The medical observation system according to claim 1, further comprising:
a second input configured to receive input of a command to stop the light source, wherein
the illumination control circuit is configured to stop the illumination light supplied by the light source when the second input receives a command to stop the light source.

8. The medical observation system according to claim 7, wherein
the light source includes:
a first light source configured to supply first illumination light having a first wavelength characteristic; and
a second light source configured to supply second illumination light having a second wavelength characteristic different from the first wavelength characteristic, and
the illumination control circuit is configured to control the second illumination light so as to be turned off or reduced when the light source supplies at least any one of the first illumination light and the second illumination light in a case where the determining circuit determines that the image sensor is outside the adjustment target range.

9. The medical observation system according to claim 7, wherein
the light source includes a blue light source configured to emit at least blue light having a blue wavelength band, and
the illumination control circuit is configured to control the blue light so as to be turned off or reduced when the light source supplies the blue light in a case where the determining circuit determines that the image sensor is outside the adjustment target range.

10. The medical observation system according to claim 1, further comprising a second-mode setting circuit configured to set, in the medical observation system, any one of an automatic adjustment mode for performing control by the illumination control circuit and a manual adjustment mode that prohibits control by the illumination control circuit in accordance with a command input from outside, wherein
the illumination control circuit is configured to control the illumination light emitted by the light source so as to be turned off or reduced when the second-mode setting circuit has set the automatic adjustment mode in the medical observation system in a case where the determining circuit determines that the image sensor is outside the adjustment target range.

11. The medical observation system according to claim 1, further comprising a notifying circuit configured to make a notification that the illumination control circuit controls the illumination light so as to be turned off or reduced.

12. The medical observation system according to claim 1, further comprising a detector configured to detect a distance from an object captured by the image sensor to a distal end part of the image sensor, wherein
the determining circuit is configured to determine whether a distance detected by the detector is less than a predetermined value, and
when the determining circuit determines that the image sensor is outside the adjustment target range when the distance is less than the predetermined value the illumination control circuit is configured to control the illumination light emitted by the light source to be turned off or reduced.

13. The medical observation system according to claim 1, further comprising an image detector configured to detect a predetermined image pattern, which is previously set, from an image that corresponds to the image signal generated by the image sensor, wherein
the determining circuit is configured to determine whether the image detector has detected the image pattern, and
when the determining circuit determines that the image sensor is outside the adjustment target range when the image detector has detected the image pattern, the illumination control circuit is configured to control the illumination light emitted by the light source to be turned off or reduced.

14. The medical observation system according to claim 1, further comprising:
a mount configured to removably hold any of different types of observation systems including at least any one of the image sensor and the light source;
a type detector configured to detect a type of the observation system attached to the mount; and
a determination control circuit configured to switch a determination function of the determining circuit to be enabled or disabled in accordance with a detection result of the type detector.

15. The medical observation system according to claim 1, further comprising:
an illumination-operation setting circuit configured to set, in the light source, any of illumination modes in which illumination parameters including an intensity, an illumination range, and flashing/non-flashing of the illumination light output by the light source are different;
a mode detector configured to detect the illumination mode set by the illumination-operation setting circuit; and
a determination control circuit configured to switch a determination function of the determining circuit to be enabled or disabled in accordance with a detection result of the mode detector.

16. The medical observation system according to claim 1, further comprising:
an illumination detector configured to detect illumination information regarding an illumination state of the illumination light output by the light source; and
an illumination-information memory configured to store the illumination information, wherein the illumination control circuit is configured to:
store, in the illumination-information memory, the illumination information previously detected by the illumination detector when the illumination light output by the light source is controlled to be reduced or turned off in accordance with a determination result of the determining circuit; and perform control to reset the illumination state of the illumination light output by the light source based on the illumination information stored in the illumination-information memory when control for reducing or turning off the illumination light output by the light source is canceled.

17. The medical observation system according to claim 1, wherein the illumination control circuit is configured to perform control such that the illumination light is output with a lowest value of a light intensity when control for reducing or turning off the illumination light output by the light source is canceled in accordance with a determination result of the determining circuit.

18. A control method implemented by a medical observation system including an image sensor that captures an object and generates an image signal; a light source that outputs illumination light in a capturing direction of the image sensor; and a support configured to hold the image sensor and the light source and movably support the image sensor and the light source, the control method comprising:
   determining a usage state of the image sensor,
   mode setting, in the medical observation system, any one of an electric visual-field move mode, in which a capturing visual field of the image sensor is changeable in upward, downward, leftward, and rightward directions by fixing a part of axes of joints included in the support and moving a different axis in accordance with a command input from outside, and an all-free mode in which the capturing direction of the image sensor is changeable by allowing rotation of the image sensor about the axis of any joint,
   controlling driving of the support in accordance with a mode set, and
   controlling illumination light emitted by the light source based on the usage state determined by the determining, and, on condition that the usage state indicates light is being output by the light source and on condition that the all-free mode is the mode set and the usage state indicates the image sensor is outside an adjustment target range, controlling the illumination light emitted by the light source to be turned off or reduced.

19. A non-transitory computer readable storage device having a program stored therein, the program causing a medical observation system including an image sensor that captures an object and generates an image signal, a light source that outputs illumination light in a capturing direction of the image sensor, and a support configured to hold the image sensor and the light source and movably support the image sensor and the light source, to execute:
   determining a usage state of the image sensor;
   mode setting, in the medical observation system, any one of an electric visual-field move mode, in which a capturing visual field of the image sensor is changeable in upward, downward, leftward, and rightward directions by fixing a part of axes of joints included in the support and moving a different axis in accordance with a command input from outside, and an all-free mode in which the capturing direction of the image sensor is changeable by allowing rotation of the image sensor about the axis of any joint;
   controlling driving of the support in accordance with a mode set; and
   controlling illumination light emitted by the light source based on the usage state determined by the determining, and, on condition that light is being output by the light source and on condition that the all-free mode is the mode set and the usage state indicates the image sensor is outside an adjustment target range, control controlling the illumination light emitted by the light source to be turned off or reduced.

* * * * *